US007612250B2

(12) United States Patent
Overstrom et al.

(10) Patent No.: US 7,612,250 B2
(45) Date of Patent: Nov. 3, 2009

(54) NUCLEAR TRANSFER EMBRYO FORMATION METHOD

(75) Inventors: Eric W. Overstrom, Grafton, MA (US); Daniela Fischer Russell, Guelph (CA)

(73) Assignee: Trustees of Tufts College, Medford, MA (US)

( * ) Notice: Subject to any disclaimer, the term of this patent is extended or adjusted under 35 U.S.C. 154(b) by 103 days.

(21) Appl. No.: 10/208,653

(22) Filed: Jul. 29, 2002

(65) Prior Publication Data
US 2004/0019924 A1    Jan. 29, 2004

(51) Int. Cl.
C12N 15/00    (2006.01)
C12N 5/00     (2006.01)
C12N 5/02     (2006.01)
(52) U.S. Cl. ......................................... 800/24; 435/325
(58) Field of Classification Search ................ 800/3, 800/8, 21, 24; 435/325
See application file for complete search history.

(56) References Cited

U.S. PATENT DOCUMENTS

| | | | |
|---|---|---|---|
| 5,496,720 A | 3/1996 | Susko-Parrish et al. | |
| 5,843,705 A | 12/1998 | DiTullio et al. | |
| 5,843,754 A | 12/1998 | Susko-Parrish et al. | |
| 5,905,042 A | 5/1999 | Stice et al. | |
| 5,945,577 A | 8/1999 | Stice et al. | |
| 5,952,222 A | 9/1999 | Rosenkrans, Jr. et al. | |
| 5,994,619 A | 11/1999 | Stice et al. | |
| 6,147,276 A | 11/2000 | Campbell et al. | |
| 6,252,133 B1 | 6/2001 | Campbell et al. | |
| 6,331,659 B1* | 12/2001 | Wakayama et al. | 800/24 |
| 6,781,030 B1* | 8/2004 | Baguisi et al. | 800/24 |
| 2002/0019993 A1 | 2/2002 | Wakayama et al. | |
| 2002/0035737 A1 | 3/2002 | Stice et al. | |
| 2005/0144663 A1 | 6/2005 | Baguisi et al. | |
| 2006/0015950 A1 | 1/2006 | Overstrom et al. | |

FOREIGN PATENT DOCUMENTS

| | | |
|---|---|---|
| GB | 2318578 A | 4/1998 |
| GB | 2331751 A | 6/1999 |
| WO | WO 95/03398 | 2/1995 |
| WO | WO 96/26268 | 9/1996 |
| WO | WO 97/07668 | 3/1997 |
| WO | WO97/07669 | 3/1997 |
| WO | WO 98/29532 | 7/1998 |
| WO | WO 99/01163 | 1/1999 |
| WO | WO 99/01164 | 1/1999 |
| WO | PCT/US99/25683 | 2/1999 |
| WO | WO 99/37143 | 7/1999 |
| WO | WO 00/25578 | 5/2000 |
| WO | WO 00/25578 A2 * | 5/2000 |
| WO | WO 00/26357 | 5/2000 |

OTHER PUBLICATIONS

Ibanez et al. Biology of Reproduction, 2003, 68:1249-1258.*
Baguisi et al. Nature, May 1999, 17:456-461.*
Lai, L. et al., "Feasibility of Producing Porcine Nuclear Transfer Embryos by Using G2/M-Stage Fetal Fibroblasts as Donors," *Biology of Reproduction*, 65:1558-1564 (2001).
Vogel, "Misguided Chromosomes Foil Primate Cloning," *Science*, 300: 225 and 227 (2003).
Simerly, "Molecular Correlates of Primate Nuclear Transfer Failures," et al., *Science*, 300: 297 (2003).
Zieve, et al., "Production of Large Numbers of Mitotic Mammalian Cells by Use of the Reversible Microtubule Inhibitor Nocodazole," *Exp. Cell Res.*, 126(2): 397-405 (1980).
Ibanez, E., et al., "Genetic Strain Variations in the Metaphase-II Phenotype of Mouse Oocytes Matured in vivo or in vitro," *Reproduction*, 130: 845-855 (2005).
Gasparrin, B., et al., "Cloned Mice Derived from Embryonic Stem Cell Karyoplasts and Activated Cytoplasts Prepared by Induced Enucleation," *Biology of Reproduction*, 68: 1259-1266 (2003).
Russell, D. Fischer, et al., "Activated Bovine Cytoplasts Prepared by Demecolcine-Induced Enucleation Support Development of Nuclear Transfer Embryos in vitro," *Molecular Reproduction and Development*, 72: 161-170 (2005).
Clayton, et al., "Control of the Surface Expression of Uvomorulin After Activation of Mouse Oocytes," *Zygote*, 3: 177-189 (May 1995).
Fulka, et al., "Chromosome Condensation Activity (CCA) in Bisected C57BL/6JXCBA Mouse Oocytes," *Reprod. Fertil. Devel.*, 7: 1123-1127 (1995).
Lessman, et al., "Movement and Dissolution of the Nucleus (Germinal Vesicle) During Rana Oocyte Meiosis: Effect of Demecolcine (Colcemid) and Centrifugation," *Gamete Res.*, 14: 11-23 (1986).
Westhusin, M.E., et al., "Nuclear Transfer in the Bovine Embryo: A Comparison of 5-day, 6-day, Frozen-Thawed, and Nuclear Transfer Donor Embryos," Granada Bioscience Inc., College Station, TX. Medline Abstract.
Westhusin, M.E., et al., "Viable Embryos and Normal Calves after Nuclear Transfer into Hoechst Stained Enucleated Demi-Oocytes of Cows," Granada Bioscience Inc., College Station, TX. Medline Abstract.
Barnes, F.L., et al., "Influence of Recipient Oocyte Cell Cycle Stage on DNA Synthesis, Nuclear Envelope Breakdown, Chromosome Constitution, and Development in Nuclear Transplant Bovine Embryos," Genmark, Inc., Salt Lakev City, UT. Medline Abstract.

(Continued)

*Primary Examiner*—Thaian N Ton
(74) *Attorney, Agent, or Firm*—Hamilton, Brook, Smith & Reynolds, P.C.

(57) ABSTRACT

A nuclear transfer embryo is formed by destabilizing microtubules of an oocyte, whereby essentially all endogenous chromatin collects at a second polar body during meiosis of an oocyte. The oocyte is fused with the nucleus of a donor somatic cell of the same species of said oocyte prior to cessation of extrusion of the second polar body from the oocyte, thereby forming the nuclear transfer embryo. In one embodiment, the nuclear transfer embryo is employed to impregnate an animal, such as a mammal. In another embodiment, the donor nucleus is transgenic.

20 Claims, 13 Drawing Sheets
(13 of 13 Drawing Sheet(s) Filed in Color)

OTHER PUBLICATIONS

Tsunoda, Y., et al., "Recent Progress and Problems in Animal Cloning," *Differentiation*, 69: 158-161 (2002).

De Sousa, P.A. et al., "Somatic Cell Nuclear Transfer in the Pig: Control of Pronuclear Formation and Integration with Improved Methods for Activation and Maintenance of Pregnancy," Biology of Reproduction, 66(3): 642-650 (Mar. 2002).

Yin, X.J. et al., "Effect of Enucleation Procedures and Maturation Conditions on the Development of Nuclear-Transferred Rabbit Oocytes Receiving Male Fibroblast Cells," Reproduction, 124: 41-47 (2002).

Westhusin, M.E., et al., "Nuclear Transfer in the Bovine Embryo: A Comparison of 5-day, 6-day, Frozen-Thawed, and Nuclear Transfer Donor Embryos," Granada Bioscience Inc., College Station, TX. Medline Abstract., 1991.

Westhusin, M.E., et al., "Viable Embryos and Normal Calves after Nuclear Transfer into Hoechst Stained Enucleated Demi-Oocytes of Cows," Granada Bioscience Inc., College Station, TX. Medline Abstract., 1992.

Barnes, F.L., et al., "Influence of Recipient Oocyte Cell Cycle Stage on DNA Synthesis, Nuclear Envelope Breakdown, Chromosome Constitution, and Development in Nuclear Transplant Bovine Embryos," Genmark, Inc., Salt Lakev City, UT. Medline Abstract., 1993.

Edwards, J.L., "Cloning Adult Farm Animals: A Review of the Possibilities and Problems Associated with Somatic Cell Nuclear Transfer," *American Journal of Reproductive Immunology*, 50: 113-123 (2003).

The Guardian, "Cloned Animals," http://www.guardian.co.uk/gall/0,8542,627251,00.html, 3 pages (Feb. 17, 2006).

Sep. 27, 2005, U.S. Preliminary Amendment, U.S. Appl. No. 11/045,872.

Apr. 10, 2007, U.S. Office Action—Restriction Requirement, U.S. Appl. No. 11/045,872.

Jul. 10, 2007, U.S. Reply to Restriction Requirement with Extension of Time by 2 months, U.S. Appl. No. 11/045,872.

Aug. 9, 2007, U.S. Office Action—Non-Final, U.S. Appl. No. 11/045,872.

Jan. 9, 2008, U.S. Amendment with Extension of Time by 3 months, U.S. Appl. No. 11/045,872.

Apr. 15, 2008, U.S. Office Action—Final, U.S. Appl. No. 11/045,872.

Jun. 30, 2008, U.S. Request for Continued Examination, Amendment and Information Disclosure Statement, U.S. Appl. No. 11/045,872.

Sep. 2, 2008, U.S. Office Action—Non-Final, U.S. Appl. No. 11/045,872.

Mar. 2, 2009, U.S. Amendment and Extension of Time by 3 months, U.S. Appl. No. 11/045,872.

Apr. 26, 2004, PCT Notification of Transmittal of the International Search Report or the Declaration, PCT/US03/23464.

Nov. 17, 2004, PCT Notification of Transmittal of International Preliminary Examination Report, PCT/US03/23464.

Mar. 17, 2005, EP Communication Pursuant to Rules 109 and 110 EPC, 03771930.9.

Feb. 21, 2008, EP Supplementary European Search Report, 03771930.9.

May 19, 2008, EP Communication Pursuant to Article 94(3) EPC, 03771930.9.

Dec. 3, 2008, EP Communication Pursuant to Rule 50(1) EPC, 03771930.9.

Nov. 26, 2008, EP Reply to Communication Pursuant to Article 94(3) EPC and Rule 71(2) EPC, 03771930.9.

May 16, 2006, Australian Official Report, 2003254208.

Jan. 25, 2008, Australian Response to Official Report, 2003254208.

Feb. 6, 2008, Australian Notice of Acceptance, 2003254208.

Jul. 31, 2006, Brazilian Petition to Request Examination (In Portuguese Language Only), PI0313159-9.

Jul. 3, 2008, Canadian Request for Examination, 2,493,187.

Sep. 15, 2008, Canadian Acknowledgement of Request for Examination, 2,493,187.

Apr. 19, 2006, New Zealand Examination Report, 537859.

Jun. 5, 2006, New Zealand Response to Examination Report, 537859.

Jun. 23, 2006, New Zealand Examination Report, 537859.

Jun. 27, 2007, New Zealand Response to Examination Report, 537859.

Nov. 19, 2007, New Zealand Examination, 537859.

Dec. 5, 2007, New Zealand Notice of Acceptance of Complete Specification, 537859.

Mar. 7, 2005, U.S. Preliminary Amendment, U.S. Appl. No. 10/913,013.

Dec. 11, 2006, U.S. Office Action—Non-Final, U.S. Appl. No. 10/913,013.

Jun. 11, 2007, U.S. Amendment with Extension of Time by 3 months and Information Disclosure Statement, U.S. Appl. No. 10/913,013.

Aug. 2, 2007, U.S. Office Action—Final, U.S. Appl. No. 10/913,013.

Jan. 2, 2008, U.S. Request for Continued Examination, Amendment and Extension of Time by 2 months, U.S. Appl. No. 10/913,013.

Mar. 20, 2008, U.S. Office Action—Non-Final, U.S. Appl. No. 10/913,013.

Jul. 9, 2008, U.S. Amendment, Extension of Time by 1 month and Information Disclosure Statement, U.S. Appl. No. 10/913,013.

Oct. 22, 2008, U.S. Office Action—Final, U.S. Appl. No. 10/913,013.

Feb. 27, 2009, U.S. Request for Continued Examination (RCE), Amendment, Extension of Time by 2 months, Terminal Disclaimer and Supplemental Information Disclosure Statement, U.S. Appl. No. 10/913,013.

Aug. 31, 2000, PCT Notification of Transmittal of the International Search Report or the Declaration, PCT/US99/25786.

Nov. 7, 2000, PCT Invitation to Restrict or to Pay Additional Fees, PCT/US99/25786.

Nov. 16, 2000, PCT Response to the Invitation to Restrict or to Pay Additional Fees, PCT/US99/25786.

Dec. 29, 2000, PCT Written Opinion, PCT/US99/25786.

Jan. 29, 2001, PCT Reply to First Written Opinion, PCT/US99/25786.

Feb. 16, 2001, PCT Notification of the Transmittal of the International Preliminary Examination Report, PCT/US99/25786.

May 22, 2003, EP Communication Pursuant to Article 96(2) EPC, 99962678.1.

Dec. 1, 2003, EP Reply to the Communication Pursuant to Article 96(2) and Rule 51(2) EPC, 99962678.1.

May 27, 2004, EP Summons to Attend Oral Proceedings on Nov. 9, 2004 Pursuant to Rule 71(1) EPC, 99962678.1.

Nov. 11, 2004, EP Withdrawal of Oral Proceedings on Dec. 9, 2004, 99962678.1.

Nov. 26, 2004, EP Communication Pursuant to Article 96(2) EPC, 99962678.1.

Mar. 23, 2005, EP Response to the Communication Pursuant to Article 96(2) and Rule 51(2), 99962678.1.

Aug. 19, 2005, EP Summons to Attend Oral Proceedings on Mar. 15, 2006 Pursuant to Rule 71(1) EPC, 99962678.1.

Feb. 15, 2006, EP Filing of Further Written Comments in Line with Rule 71(1) EPC, 99962678.1.

Feb. 23, 2006, EP Result of the Feb. 20, 2006 Consultation by Telephone with the Applicant/Representative, 99962678.1.

Mar. 8, 2006, EP Submittal of New Auxiliary Request and Molecular Reproduction and Development article, 99962678.1.

Mar. 13, 2006, EP Submittal of New pp. 2, 3, 4 and 5 of the Description, 99962678.1.

Mar. 14, 2006, EP Withdrawal of Oral Proceedings on Mar. 15, 2006, 99962678.

Jun. 8, 2006, EP Communication Under Rule 51(4) EPC, 99962678.1.

Mar. 21, 2007, EP Certificate of Grant, 99962678.1.

Oct. 24, 2006, Japanese Request for Examination and Amendment (Request for Examination and Body of Amendment in Japanese Language Only; English Translation of Claim Amendment Provided), 2000-579047.

Jul. 11, 2007, EP Extended Search Report, 06025537.9.

Mar. 13, 2008, EP Communication Pursuant to Article 94(3) EPC, 06025537.9.

Sep. 16, 2008, EP Reply to the Communication Pursuant to Article 94(3) EPC and Rule 71(2) EPC, 06025537.9.

Fischer, et al., "Activated Bovine Cytoplasts Produced by Induced Enucleation Support Development of Bovine Nuclear Transfer Embryos in Vitro," *Society for the Study of Reproduction, 35th Annual Meeting*, Baltimore, MD (Jul. 2002).

Ibanez, E., et al., "Demecolcine-Induced Oocyte Enucleation for Somatic Cell cloning: Coordination Between Cell-cycle Egress, Kinetics of Cortical Cytoskeletal Interactions, and Second Polar Body Extrusion," *Biology of Reproduction*, 68: 1249-1258 (2003).

Ibanez, E., "Induced enucleation of Mouse and goat Oocytes: Kinetic and Phenotypic Characterzations," *Theriogenology*, Jan. 2001, Abstract No. 421.

Baguisi, A., et al., "Production of goats by somatic cell nuclear transfer," *Nature Biotechnology*, 17: 456-461 (1999).

Baguisi A. et al., "Induced Enucleation in Nuclear Transfer Procedures to Produce Cloned Animals," *Theriogenology*, 54:209 (2000).

Bordignon, V. and Smith, L.C., "Telophase enucleation: an improved method to prepare recipient cytoplasts for use in bovine nuclear transfer," *Molecular Reproduction and Development*, 49:29-36 (1998).

Meinecke-Tillman, S, "Experimental Chimaeras—Removal of Reproductive Barrier Between Sheep and Goat," *Nature*, 307: 637-638 (1984).

Wu, B. et al., "Dynamics of Maturation-Promoting Factor and its Constituent Proteins During in Vitro maturation of Bovine Oocytes," *Biology of Reproduction*, 56: 253-259 (1997).

Ebert, K.M., et al., "Transgenic production of a Variant of Human Tissue-type Plasminogen Activator in Goat Milk: Generation of Transgenic goats and analysis of Expression," 9: 835-838 (1991).

Cibelli, J.B., et al., "Cloned Transgenic Calves Produced from Nonquiescent Fetal Fibroblasts", *Science*, 280:1256-1258 (1998).

Robl, J.M., et al., "Somatic Cell Nuclear Transplantation in Cattle," Annual Meeting Soc. Study Reprod., vol. 58, (Aug. 8, 1998), p. 25.

Gordon, K., et al., "Production of Human Tissue Plasminogen Activator in Transgenic Mouse Milk," *Bio/Technology*, 5: 1183-1187 (p. 1186 is an advertisement) (1987).

Yin, X. J., at al., "Production of Cloned Pigs from Adult Somatic Cells by Chemically Assisted Removal of Maternal Chromosomes," *Biology of Reproduction*, 67: 442-446 (2002).

Yong, Z., et al., "Nuclear-Cytoplasmic Interaction and Development of Goat Embryos Reconstructed by Nuclear Transplantation: Production of Goats by Serially Cloning Embryos", *Biology of Reproduction*, 58:266-269 (1998).

Shu H-B et al., A Transient Association of γ-tubulin at the Midbody is Required for the Completion of Cytokinesis During the Mammalian Cell Division, *J. Cell. Sci.*, 108:2955-2962 (1995).

Campbell, K.H.S., et al., "Sheep cloned by nuclear transfer from a cultured cell line", *Nature*, 380:64-66 (1996).

Campbell, K.H.S., et al., "Featured Article: Cloning Farm Animals by Nuclear Transfer: From Cell Cycles to Cells", *Embryo Transfer Newsletter*, 14(1):12-16 (1996).

Savoian MS et al., "Cleavage Furrows Formed Between Centrosomes Lacking an Intervening Spindle and Chromosomes Contain Microtubule Bundles, INCENP and CHO1 but not CENP-E," *Mol. Biol. Cell*, 10:297-311 (1999).

Wilmut, I., et al., "Viable offspring derived from fetal and adult mammalian cells", *Nature*, 385:810-813 (1997).

Wolf, D.P., et al., "Nuclear transfer in the rhesus monkey: practical and basic implications," *Biology of Reproduction*, 60:199-204 (1999).

Fulka, Jr., J. and Moor, R.M., "Noninvasive chemical enucleation of mouse oocytes," *Molecular Reproduction and Development*, 34:427-430 (1993).

Procházka, R. and Fiser, P.S., "Behavior of blastomere nuclei fused to mouse oocytes is affected by oocyte enucleation and age," *Reprod. Nutr. Dev.*, 39:695-701 (1995).

Kárníková, L., et al., "Chemically enucleated mouse oocytes: ultrastructure and kinetics of histone H1 kinase activity," *Reprod. Nutr. Dev.*, 38:643-651 (1998).

Campbell, K.H.S., "Nuclear transfer in farm animal species," *Cell & Developmental Biology*, 10:245-252 (1999).

Zawada, W.M., et al., "Somatic cell cloned transgenic bovine neurons for transplantation in parkinsonian rats," *Nature Medicine*, 4:569-574 (1998).

Stice, S.L., et al., "Cloning: new breakthroughs leading to commercial opportunities," *Theriogenology* 49:129-138 (1998).

Rampoldi, E., et al. "Cytologic and flow cytometric DNA analysis of multinucleated tumor cells and derived microcells," *Analytical and Quantitative Cytology and Histology*, 11:59-66 (1989).

Lanza, R.P., et al., "Human therapeutic cloning," *Nature Medicine*, 5:975-977 (1999).

Lanza, R.P., et al., "Prospects for the use of nuclear transfer in human transplantation," *Nature Biotechnology*, 17: 1171-1174 (1999).

Cibelli, J.B., et al., "Transgenic bovine chimeric offspring produced from somatic cell-derived stem-like cells," *Nature Biotechnology*, 16:642-646 (1998).

Tanaka, H., et al., "Influence of Time After the Removal of Nocodazole from Nuclear Donors on the Development of Reconstituted Embryos in Bovine Nuclear Transplantation," *Jpn. J. Vet. Res.*, 43(3-4):135-143 (1995).

Prather, R.S., et al., "Cloning Embryos by Nuclear Transfer," *J. Reprod. Fert., Suppl.*, 41:125-134 (1990).

Campbell, K.H.S., et al., "Cell Cycle Co-ordination in Embryo Cloning by Nuclear Transfer," *Reviews of Reproduction*, 1:40-46 (1996).

Gorgidze, L.A., et al., "Centrosome and Microtubules Behavior in the Cytoplasts," *J. Submicrosc. Cytol. Pathol.*, 27(3):381-389 (1995).

Liu, L., et al., "Nuclear Transfer in Sheep Embryos: The Effect of Cell-Cycle Coordination Between Nucleus and Cytoplasm and the Use of In Vitro Matured Oocytes," *Molecular Reproduction and Development*, 47:255-264 (1997).

Kanka, J., et al., "Nucleolar Ultrastructure in Bovine Nuclear Transfer Embryos," *Molecular Reproduction and Development*, 52(3):253-263 (1999).

Kono, T., "Nuclear Transfer and Reprogramming," *Reviews of Reproduction*, 2(2):74-80 (1997).

Pinto-Correia, C., et al., "Embryo Development: Factors Involved in Nuclear Reprogramming During Early Development in the Rabbit," *Molecular Reproduction and Development*, 40(3):292-304 (1995).

Campbell, K.H.S., et al., "Nuclear-Cytoplasmic Interactions During the First Cell Cycle of Nuclear Transfer Reconstructed Bovine Embryos: Implications for Deoxyribonucleic Acid Replication and Development," *Biology of Reproduction*, 49(5):933-942 (1993).

Collas, P., et al., "Influence of Cell Cycle Stage of the Donor Nucleus on Development of Nuclear Transplant Rabbit Embryos," *Biology of Reproduction*, 46(3):492-500 (1992).

Kanka, J., "Nuclear Transplantation: Reprogramming of Transplanted nuclei," *Reprod. Nutr. Dev.*, 39(5-6):545-554 (1999).

Collas, P., et al., "Effect of Donor Cell Cycle Stage on Chromatin and Spindle Morphology in Nuclear Transplant Rabbit Embryos," *Biology of Reproduction*, 46(3):501-511 (1992).

Wakayama, T., et al., "Mice Cloned from Embryonic Stem Cells," *PNAS*, 96(26):14984-14989 (1999).

Kubota, C., et al., "Six Cloned Calves Produced from Adult Fibroblast Cells After Long-term Culture," *Proc. Natl. Acad. Sci. USA*, 97(3):990-995 (2000).

Wheatley SP et al., "CDK1 Inactivation Regulates Anaphase Spindle Dynamics and Cytokinesis in vivo," *J. Cell. Biol.* 138:385-393 (1997).

Campbell, K.H.S., et al., "Sheep cloned by nuclear transfer from a cultured cell line," *Nature 380*:64-66 (1996).

Liu, L., et al., "Nuclear remodeling and early development in cryopreserved, porcine primordial germ cells following nuclear transfer into in vitro-matured oocytes," *Int. J. Dev. Biol.* 39:639-644 (1995).

Presicce, G.A. and Yang, X., "Parthenogenetic Development of Bovine Oocytes Matured In Vitro for 24 Hr and Activated by Ethanol and Cycloheximide," *Molecular Reproduction and Development* 38:380-385 (1994).

Schnieke, A.E., et al., "Human Factor IX Transgenic Sheep Produced by Transfer of Nuclei from Transfected Fetal Fibroblasts," *Science 278*:2130-2133 (1997).

Vignon, X., et al., "Developmental potential of bovine embryos reconstructed from enucleated matured oocytes fused with cultured somatic cells," *Life Sciences 321*:735-745 (1998).

Wakayama, T., et al., "Full-term development of mice from enucleated oocytes injected with cumulus cell nuclei," *Nature 394*:369-374 (1998).

Wilmut, I., et al., "Viable offspring derived from fetal and adult mammalian cells," *Nature* 385:810-813 (1997).

Clark, et al., "Expression of Human Anti-Hemophilic Factor IX in the Milk of Transgenic Sheep," *Biotechnology*, 7: 487-492 (1989).

Soulier, et al., "Expression Analysis of Ruminant α-lactalbumin in Transgenic Mice: Developmental Regulation and General Location of Important *cis*-regulatory Elements," Febs Letts., 297: (No. 1, 2), 13-18 (1992).

DiTullio, "Production of Cystic Fibrosis Transmembrane Conductance Regulator in the Milk of Transgenic Mice," *Bio/Technology*, 10: 74-77 (1992).

Wells, D. N., et al., "Production of Cloned Calves Followinig nuclear Transfer With Cultured Adult Mural Granulosa Cells," *Biol. Reprod.*, 60: 996-1005 (1999).

Betthauser, J., et al. "Production of Cloned Pigs from In Vitro Systems," *Nature Biotechnology*, 18:1055-1059 (2000).

Onishi, A. et al., "Pig Cloning by Microinjection of Fetal Fibroblast Nuclei," *Science*, 289:1188-1190 (2000).

Polejaeva, IA et al., "Cloned Pigs Produced by Nuclear Transfer from Adult Somatic Cells," *Nature*, 407:86-90 (2000).

Elsheikh AS et al., "Developmental Ability of Mouse Late 2-Cell Stage Blastomeres Fused to Chemically Enucleated Oocytes in vitro," *J. Vet. Med. Sci.*, 59:1077-10113 (1997).

Elsheikh AS et al., "Functional Enucleation of Mouse Metaphase II Oocytes with Etoposide," *Jpn. J. Vet. Res.*, 45:217-220 (1998).

Presicce and Yang, "Nuclear Dynamics of Parthenogenesis of Bovin Oocytes Matured in Vitro for 20 and 40 Hours and Activated with combined Ethanol and Cycloheximide Treatment," *Molecular Reproductive Development*, 37: 61-68 (1994).

Biggers JD et al., "Amino Acids and Preimplantation Development of the Mouse in the Protein-Free KSOM," *Biol. Reprod.*, 63:281-293 (1998).

Wickcramasinghe D et al., "Centrosome Phosphorylation and the Developmental Expression of Meiotic Competence in Mouse Oocytes," *Dev. Biol.*, 152:62-74 (1992).

Liu L. et al., "Increased Birefringence in the Meiotic Spindle Provides a New Marker for the Onset of Activation in Living Oocytes," *Biol. Reprod.*, 63:251-258 (2000).

Kubiak JZ et al., "The Metaphase II Arrest in Mouse Oocytes is Controlled through Microtubule-Dependent Destruction of Cyclin B in the Presence of CSF," *EMBO J.*, 12:3773-3778 (1993).

Winston NJ et al., "The Exit of Mouse Oocytes from Meiotic M-Phase Requires an Intact Spindle During Intracellular Calcium Release," *J. Cell. Sci.*, 108:143-151 (1993).

Moses R. et al., "Maintenance of Metaphase in Colcemid-treated Mouse Eggs by Distinct Calcium- and 6- dimethylaminopurine (6-DMAP)-sensitive machanisms," *Dev. Biol.*, 167:329-337 (1995).

Ilyin V. et al., "Effects of Alcohols on Responses Evoked by Inositol Trisphosphate in Xenopus Oocytes," *J. Physiol*, 448:339-354 (1992).

Combelles CM et al., "Microtubule Patterning During Meiotic Maturation in Mouse Oocytes is Determined by Cell Cycle-Specific Sorting and Redistribution of γ-tubulin," *Dev. Biol.*, 239:281-294 (2001).

Maro B. et al., "Changes in Actin Distribution During Fertilization of the Mouse Egg," *J. Embryol. Exp. Morph.*, 81:211-237 (1984).

Gard DL et al., "Confocal Immununofluorescence Microscopy of Microtubules, Microtubule-Associated Proteins, and Microtubule-Organizing Centers During Amphibian Oogenesis and Early Development," *Curr. Top. Dev. Biol.*, 31:383-431 (1995).

Carabatsos MJ et al., "Sorting and Reorganization of Centrosomes during Oocyte Maturation in the Mouse," *Microsc. Res. Tech.*, 49:435-444 (2000).

Larkin K. et al., "Microtubules are Required for Completion of Cytokinesis in Sea Urchin Eggs," *Dev. Biol.* 214:215-226 (1999).

Wheatley SP et al., "Midzone Microtubule Bundles are Continuously Required for Cytokinesis in Cultured Epithelial Cells," *J. Cell. Biol.*, 135:981-989 (1996).

Glotzer M., "Animal Cell Cytokinesis," *Annu. Rev. Cell. Dev. Biol.*, 17:351-386 (2000).

Cao L-G et al., "Signals from the Spindle Midzone are Required for the Stimulation of Cytokinesis in Cultured Epithelial Cells," *Mol. Biol. Cell.*, 7:225-232 (1996).

Danilchik MV et al., "Requirement for Microtubules in New Membrane Formation During Cytokinesis of *Xenopus* Embryos," *Dev. Biol.*, 194:47-60 (1998).

Mitsuyama F. et al., "The Redistribution of $Ca^{2+}$-stores with Inositol 1,4,5-trisphosphate Receptor to the Cleavage Furrow in a Microtubule-dependent Manner," *Int. J. Dev. Biol.*, 45:861-868 (2001).

Julian M. et al., "γ-Tubulin Participates in the Formation of the Midbody During Cytokinesis in Mammalian Cells," *J. Cell. Sci.*, 105:145-156 (1993).

\* cited by examiner

NUCLEAR TRANSFER EMBRYO FORMATION METHOD

GOVERNMENT SUPPORT

This invention was supported, in whole or in part, by Grant No. 2001-35205-09966 from the United States Department of Agriculture. The Government has certain rights in the invention.

BACKGROUND OF THE INVENTION

Nuclear transfer methods have been developed and used successfully to produce cloned sheep, cattle, mice, goats and pigs. Two cell components are combined to produce a cloned embryo; the donor nuclear genome (karyoplast) that is the target for clonal replication, and the enucleated oocyte (cytoplast) whose cytoplasmic constituency is sufficiently competent to facilitate genome reprogramming and support embryonic development to term.

Mammalian oocyte cytoplasts have been prepared by physically removing nuclear chromatin by micromanipulation techniques in preparation to receive the donor genome. Enucleated oocytes arrested at metaphase of meiosis II (MII) are subsequently "reconstructed" by the addition of the donor karyoplast typically using either electrofusion or microinjection techniques. However, physical enucleation is generally technically demanding, time consuming, inherently invasive and clearly damaging to cytoplast spatial organization. Moreover, in certain instances, development of reconstructed embryos is inherently inefficient.

One alternative strategy to physical enucleation has been to treat oocytes with agents that modify the processes of karyokinesis and cytokinesis and result in chemically enucleated oocytes at high rates (>85%). However, certain studies have reported that exposure of metaphase I and MII oocytes to etoposide, a topoisomerase II inhibitor, and cycloheximide yields enucleated cytoplasts with limited ability to support cleavage or blastocyst development, and term development of reconstructed embryos has not been reported.

Hence, a need exists for improved methods for developing nuclear transfer embryos.

SUMMARY OF THE INVENTION

The present invention relates to methods of forming a nuclear transfer embryo by destabilizing microtubules of an oocyte (e.g., mammalian (human or non-human)), whereby essentially all endogenous chromatin collects at (e.g. segregates into) a second polar body during meiosis of the oocyte. The methods also include combining the oocyte with at least the nucleus of a donor cell of the same species of the oocyte prior to cessation of extrusion of the second polar body from the oocyte, thereby forming a nuclear transfer embryo. Certain conditions and/or compounds destabilize the microtubules of the meiotic spindle of the oocyte. Examples of chemicals that destabilize the microtubules of the oocyte include demecolcine, paclitaxel, phalloidin, colchicine, and nocodozole. Such conditions include alterations (e.g., increasing or decreasing) in electromagnetic radiation (e.g., x-rays or heat), pH or osmolality.

In one embodiment, the present invention further includes activating the oocyte prior to exposing the oocyte to the chemical that induces enucleation. Stages of an activated oocyte include telophase II or anaphase II stage of meiosis. In another embodiment, the oocyte is in a resting of meiosis (e.g., metaphase II stage) during injection of the donor nucleus.

The present invent utilizes donor cell that are in various stages of mitotic cell cycle, and can include several types of cells. The present invention encompasses use of an active (e.g., $G_1$, S or $G_2$/M stage of a mitotic cell cycle) or inactive (e.g., $G_0$ stage of a mitotic cell cycle) donor cell. The donor cell can be an active or inactive fibroblast cell, epithelial cell, a somatic cell (e.g., adult or embryonic). The donor cell can also be transgenic.

The present invention also encompasses methods for cloning a mammal by forming the nuclear transfer embryo, as described herein, and impregnating a mammal of the same species as the nuclear transfer embryo with the nuclear transfer embryo under conditions suitable for gestation of the cloned mammal; and gestating the embryo, thereby causing the embryo to develop into the cloned mammal.

The present invention further includes methods for producing a transgenic mammals, by forming a nuclear transfer embryo using a transgenic donor cell, as described herein, and impregnating a mammal of the same species as the nuclear transfer embryo with the nuclear transfer embryo under conditions suitable for gestation of the transgenic mammal; and gestating the embryo, thereby causing the embryo to develop into the transgenic mammal.

Yet another embodiment of the invention includes methods for cloning a mammalian fetus, by forming a nuclear transfer embryo as described herein, and impregnating a mammal of the same species as the nuclear transfer embryo with the nuclear transfer embryo under conditions suitable for gestation of the cloned mammalian fetus; and gestating the embryo, thereby causing the embryo to develop into the cloned mammalian fetus.

The present invention further pertains to methods of producing a protein of interest in an animal, by forming a nuclear transfer embryo as described herein, and impregnating a mammal of the same species as the nuclear transfer embryo with the nuclear transfer embryo under conditions suitable for gestation of the cloned mammal; gestating the embryo, thereby causing the embryo to develop into the cloned mammal; and purifying the protein of interest (e.g., tissue, cells or a bodily secretion) from the cloned animal. Examples of sources from which proteins that can be purified from cloned animals include milk, blood, urine, hair, mammary gland, muscle, viscera (e.g., brain, heart, lung, kidney, pancreas, gall bladder, liver, stomach, eye, colon, small intestine, bladder, uterus and testes).

The present invention also relates to methods of producing a heterologous protein in a transgenic animal by forming a transgenic nuclear transfer embryo, as described herein, and impregnating a mammal of the same species as the nuclear transfer embryo with the nuclear transfer embryo under conditions suitable for gestation of a transgenic cloned mammal; gestating the embryo, thereby causing the embryo to develop into the transgenic cloned mammal; and purifying the protein of interest from the transgenic cloned animal. In one embodiment, the genetically engineered nucleus includes an operatively linked promoter (e.g., a host endogenous promoter, an exogenous promoter and a tissue-specific promoter (e.g., mammary-specific promoter, blood-specific promoter, muscle-specific promoter, neural-specific promoter, skin-specific promoter, hair-specific promoter and urinary-specific promoter)).

In another embodiment, the present invention relates to methods of forming a nuclear transfer embryo by performing the steps in the following order: combining an oocyte with at least the nucleus of a donor cell of the same species of the oocyte; activating the oocyte; and destabilizing microtubules of the oocyte, whereby essentially all endogenous chromatin collects at a second polar body during meiosis of the oocyte, thereby forming a nuclear transfer embryo. The oocyte can be in a metaphase II stage of meiosis prior to activation, or in a telophase II or anaphase II stage of meiosis after activation.

The present invention also includes methods of forming a nuclear transfer embryo, by activating an oocyte; combining the activated oocyte with at least the nucleus of a donor cell of the same species of the oocyte in less than about 45 minutes (e.g., 40, 35, 30, 25, 20, 15, 10 or 5 minutes) after activation of the oocyte; and destabilizing microtubules of the activated oocyte, whereby essentially all endogenous chromatin collects at a second polar body during meiosis of the oocyte, thereby forming a nuclear transfer embryo.

The methods of the invention have advantages over methods of nuclear transfer that employ mechanical enucleation (e.g., enucleation using a micropipette to remove the nucleus) of the oocyte for several reasons. For example, using physical enucleation, the nucleus along with other important spindle associated elements are also removed. These spindle associated elements include, for example, centrosome factorsn α-tubulin, pericentrin), kinases (e.g., C-mos, MPF, PAPK) and competence factors (e.g., cdc25C, spindlin). Several of these elements are important in forming a nuclear transfer embryo that is developmentally competent (e.g., embryo's ability or likelihood to develop successfully in vivo following an embryo transfer and implantation to a recipient mammal). The method of the invention removes the endogenous nucleus from the oocyte, while allowing several of these spindle associated elements to remain in the oocyte, thereby potentially significantly improving yield of competent embryos.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A is a series of two photographs (A1 and A2) showing a control activated oocyte at telophase II extruding a second polar body (PB). FIG. 3B is a series of two photographs (B1 and B2) showing activated demecolcine-treated oocyte showing two sets of chromosomes connected by spindle remnants, and two cortical protrusions. FIG. 3C is a series of two photographs (C1 and C2) showing a single group of chromosomes and no MTs in which demecolcine-treated oocyte that failed to activate. Note the bright green appearance in the cytoplasm of the demecolcine treated oocytes shown B1, C1 as compared to A1, is due to MT depolymerization. For each oocyte, microtubules (green) and chromatin (blue, H2258) staining patterns are shown on the left (A1-C1), and microfilaments (red, rhodamine pholloidin) staining pattern is shown on the right (A2-C2). First PBs are not visible in any of the oocytes.

FIG. 4A is a set of two photographs (A1 and A2) showing the meiotic spindle of a metaphase II oocyte prior to activation. FIG. 4B is a set of two photographs (B 1 and B2) showing onset of meiotic spindle rotation of a metaphase II oocyte prior to activation 30 minutes postactivation. FIG. 4C is a set of two photographs (C1 and C2) showing final perpendicular orientation of meiotic spindle rotation of a metaphase II oocyte after activation. For each oocyte, microtubules (green) and chromatin (blue, H258) staining patterns are shown on the left (A1-C1), and microfilaments (red, rhodamine pholloidin) staining pattern is shown on the right (A2-C2). Arrowheads indicate the presence of the first PB (PB 1).

FIG. 5A is a set of two micrographs (A1 and A2) showing a single (type A oocyte) cortical protrusions overlying the two sets of chromosomes and the remnants of the spindle. FIG. 5B is a set of two micrographs (B1 and B2) showing a double (type B oocyte) cortical protrusions overlying the two sets of chromosomes and the remnants of the spindle. For each oocyte, microtubules (green) and chromatin (blue, H258) staining patterns are shown on the left (A1, B1), and microfilaments (red, rhodamine pholloidin) staining patterns are shown on the right (A2, B2). Arrowhead indicates the presence of the first PB, out of focus.

FIG. 6A shows the time course for complete second PB extrusion for B6D2F1 strain mouse oocytes, and FIG. 6B shows the time course for complete second PB extrusion for CF-1 strain mouse oocytes. Oocytes were analyzed by immunofluorescence at several time-points after activation to assess the extent and completeness of second PB extrusion. Different superscripts represent significant differences ($P<0.05$) between different treatments for each time-point and strain.

FIGS. 7A-7B show demecolcine-treated oocytes at 135 min post-activation with one first PB (arrowhead) and two partially extruded second PBs. FIG. 7A is a micrograph showing an oocyte with microtubules (green) and chromatin (blue, H258) staining patterns. FIG. 7B is a micrograph of an oocyte stained to reveal microfilaments. All the oocyte chromatin is enclosed in the two cortical protrusions, that show some degree of constriction at the oolema. FIG. 7C is a series of color photographs showing the phenotypes with and without extruded second PB (Type A, Type B, Type C (Control), Type D, Type E, and Type F) of mouse oocytes that were treated with demecolcine.

FIG. 8A shows a control activated type C oocyte, while FIG. 8B (Type D), FIG. 8C (Type E) and FIG. 8D (Type F) correspond to activated oocytes treated with demecolcine. Oocytes in FIGS. 8C and 8D are fully enucleated. Arrowheads indicate the presence of the first PB.

FIG. 10A shows the percentage of enucleated oocytes of only those activated oocytes that completed second PB extrusion, and FIG. 10B shows the total of activated oocytes. The value in each treatment represents the combined results for all four time-points examined (45, 75, 105 and 135 min p.a.). Different superscripts represent significant differences ($P<0.05$) between treatments for each strain of oocytes. In both FIGS. 10A and 10B, values for each treatment differ significantly between strains.

DETAILED DESCRIPTION OF THE INVENTION

Figure 1:
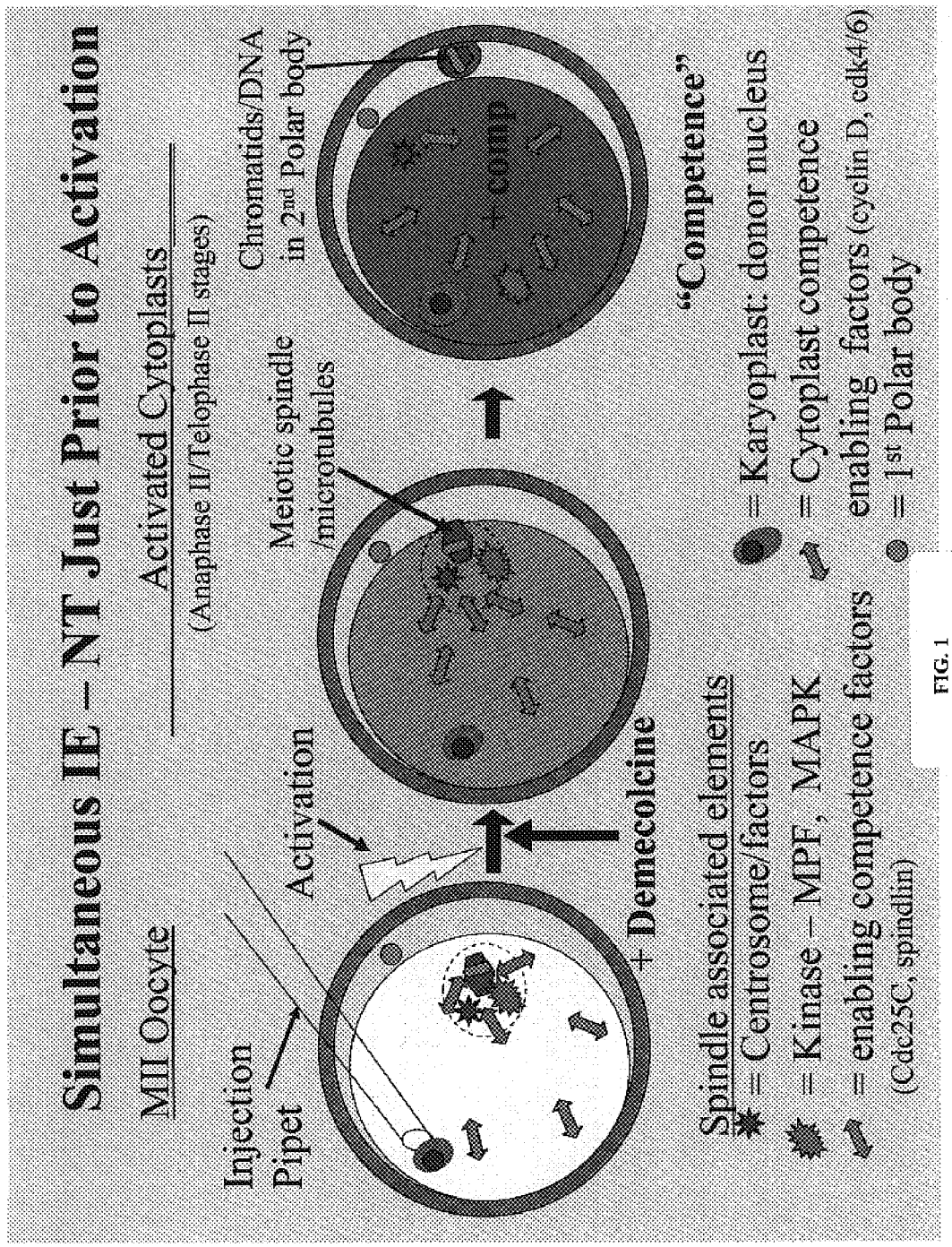
FIG. 1 is a schematic diagram showing the process of induced enucleation and the introduction of the donor nucleus before extrusion of the second polar body containing essentially all endogenoses chromatin of the oocyte ceases.

The present invention relates to new methods of cloning animals by enucleating an oocyte by induced enucleation and, prior to the cessation of protrusion of a second polar body containing essentially all of endogenous chromatin of the oocyte (e.g., the completion of the enucleation), combining (e.g., injecting or fusing) at least the nucleus from a somatic donor cell (e.g., karyoplast) with the oocyte. The nuclear material from the somatic donor cell is combined with the oocyte (e.g., cytoplast) before the protrusion of the second polar body containing essentially all of the endogenous chromatin ceases.

The present invention utilizes "induced enucleation" which refers to enucleation of the oocyte by disrupting the meiotic spindle apparatus through the destabilization (e.g., depolymerization) of the microtubules of the meiotic spindle. Destabilization of the microtubules prevents the chromatids from separating (e.g., prevents successful karyokinesis), and induces the oocyte genome (e.g., nuclear chromatin) to segregate unequally (e.g., skew) during meiotic maturaton, whereby essentially all endogenous chromatin of the oocyte collects in the second polar body.

Induced enucleation can be accomplished, for example, by exposing an oocyte with compounds or conditions (e.g., at least one compound and/or condition) that destabilize the microtubules, as described above. Examples of compounds that destabilize the microtubules include, but are not limited to, demecolcine, Taxol® (e.g., paclitaxel), phalloidin, colchicine, and nocodozole. Methods of chemically inactivating the DNA are known to those of skill in the art. Completion of enucleation can be determined by visually inspecting oocyte having stained microfilaments e.g., with rhodamine pholloidin. In addition, exposure of oocytes to certain conditions (e.g. increased or decreased temperature, pH, osmolality) that induce destabilization of the microtubules. In particular, oocytes are exposed to temperatures, pH and/or osmolality that are above or below normal body conditions for that species.

Before the enucleation process is completed, the nucleus (e.g., genome) from the donor cell is introduced into the oocyte. Completion of enucleation is signified by the cessation of the second polar body extrusion (e.g., completion of cytokinesis or effective cessation of active, or observable, continuing extrusion of the second polar body). For example, a compound, such as demecolcine, which destabilizes microtubules can, depending upon the concentration employed, slow extrusion of a second polar body to effectively terminate continuing extrusion and, thereby, prevent completion of cytokinesis which, normally would mark the end point of second polar body formation. The second polar body (PB), in the case of induced enucleation, contains all of the endogenous nuclear chromatin (e.g., the nucleus) of the oocyte. The introduction of the donor nucleus can occur before, during or shortly after the enucleation process begins (e.g., after exposure to the compound or condition that induces enucleation), but before the cessation of the second PB extrusion containing the nucleus of the oocyte. Representative examples of complete second PB extrusion, induced chemically with demecolcine, is shown in the Exemplification. Preferably, the second PB is fully extruded and contains the nuclear chromatid of the oocyte. However, in some instances the second PB is not fully extruded. Figures recited in the Exemplification show that in some instances, although enucleation is completed and the second PB is formed, the second PB is not fully extruded in all cases. Regardless of the extent to which extrusion of the second PB actually occurs, the end point for the completion of the enucleation process is cessation of extrusion of a second PB containing essentially all endogenous nuclear chromatin of the oocyte. Additionally, induced enucleation was performed on mouse, goat and bovine embryos, and for each species demecolcine caused the enucleation of the oocyte to form a second PB containing essentially all of the endogenous chromatin of the oocyte. See Exemplification.

When using a compound that destabilizes the microtubules to enucleate an oocyte, the induced enucleation begins upon exposure of the compound and continues until the protrusion of a second polar body containing essentially all endogenous chromatin ceases, such as by completing formation of the second polar body. The length of time needed to complete enucleation depends on a variety of factors including the specific compound or condition used for the enucleation, and the species or strain within a species of oocyte used. In general, induced enucleation for mammals using demecolcine is about 5 hours post-activation. For example, when using demecolcine to enucleate bovine oocytes, induced enucleation (greater than 80%) generally requires about 5 hours post-activation. Induced enucleation with demecolcine generally takes about 1.5 hours for murine oocytes (greater than 50%), 4-6 hours for pig oocytes, 3-5 hours for human oocytes, and 5 hours for goat oocytes (greater than 80%). One of skill in the art can readily determine the length of time required to complete induced enucleation.

Activated oocytes are those that are in a dividing stage of meiotic cell division, and can include any meiotic phase except metaphase II (e.g., metaphase I, anaphase I, telophase I, and preferably, anaphase II and telophase II) stage. In particular, activated oocytes refer to those metaphase II oocytes that have been stimulated to resume meiosis naturally (e.g., fertilization) or by artificial means (e.g., ethanol, ionomycin, electrical change, or chemical activation). An activated oocyte is also defined as one that has a protruding second polar body. Oocytes in metaphase II are considered to be in a resting state and are therefore arrested. The oocytes can be in the resting stage of metaphase II, and then activated, using methods described herein. The stage that the oocyte is in can be identified by visual inspection of the oocyte under a sufficient magnification. Methods for identifying the stage of meiotic cell division are known in the art.

In another embodiment, the oocyte can be quiescent, in metaphase II. In accordance with the present invention, the donor nucleus is introduced to the metaphase II oocyte and then activated. See FIG. 1. Once the metaphase II oocyte and the donor nucleus is combined, the oocyte is activated and enucleation of the endogenous nucleus is induced, as described herein, to thereby form a nuclear transfer embryo. This nuclear transfer embryo is ready to be implanted into an animal that is of the same as the embryo.

Figure 2:
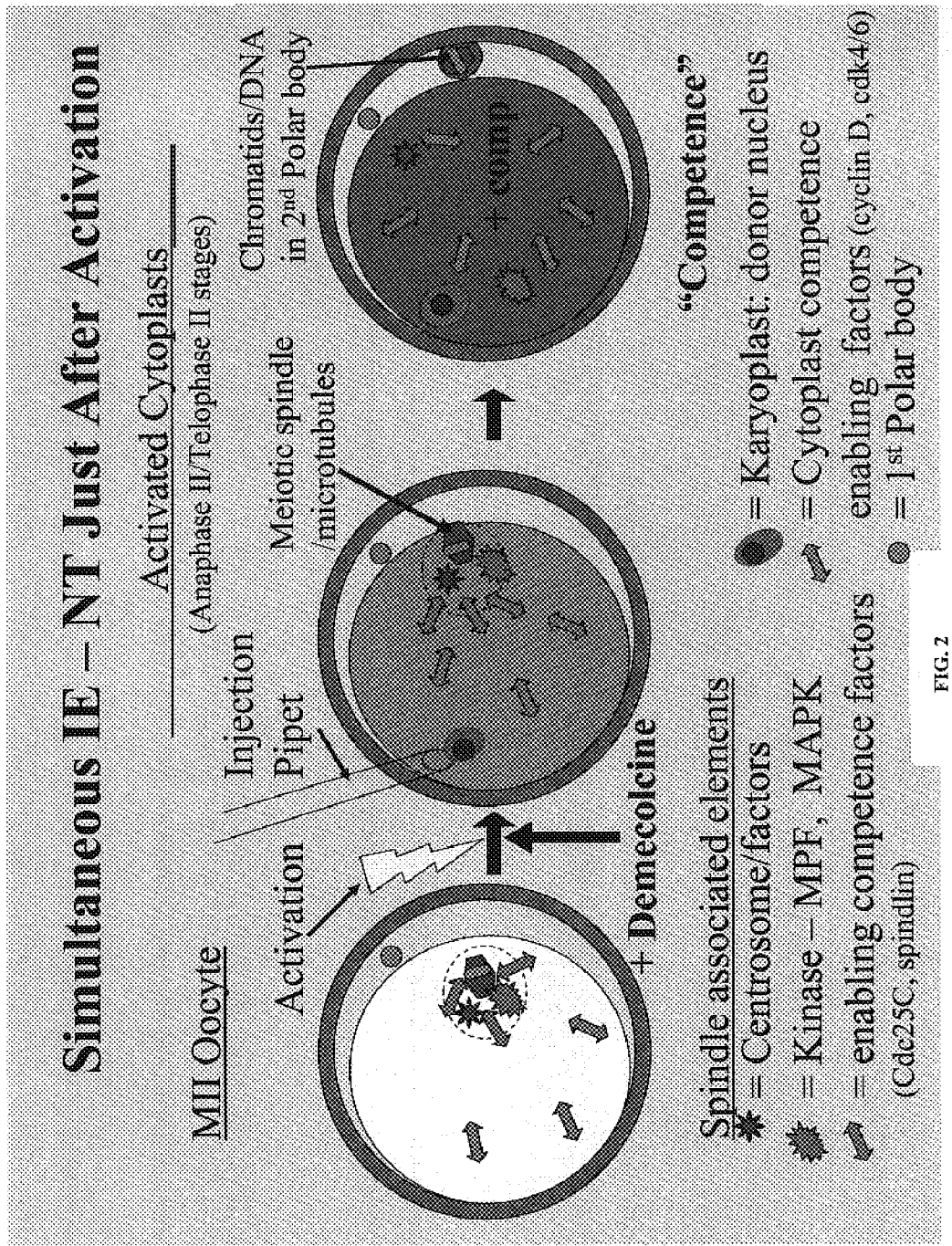
FIG. 2 is a schematic diagram showing the process of induced enucleation and the introduction of the donor nucleus before cessation of extrusion of the second polar body containing essentially all of the chromatin of a telophase II oocyte.

In one embodiment, the oocyte can be activated prior to exposure to a microtubule destabilizing compound. For example, an activated oocyte can be in the anaphase II or telophase II stage of meiotic cell division, and then exposed to the microtubule destabilizing compound. Before enucleation is complete, the donor nucleus is introduced to the active, enucleated oocyte. See FIG. 2. This process forms a nuclear transfer embryo which is ready to be implanted into an animal that is of the same species as the embryo.

Oocytes are activated by, for example, increasing their exposure to calcium levels. Increasing levels of calcium, e.g., by between about 10% and about 60% above the baseline levels, induces activation or meiotic cell division of the oocyte. Baseline levels are those levels of calcium found in an inactive oocyte. Rising levels of calcium, coupled with decreasing levels of phosphorylation further facilitates and sustains activation of the oocyte. Several methods exist that allow for activation of the oocyte. In particular, a calcium ionophore (e.g., ionomycin) is an agent that increases the permeability of the oocyte's membrane and allows calcium to enter into the oocyte. As the free calcium concentration in the cell increases during exposure to the ionophore, the oocyte is activated following reduction in MPF (maturation promoting factor) activity. Such methods of activation are described in U.S. Pat. No. 5,496,720. Ethanol has a similar affect. Prior to or following enucleation, an oocyte in metaphase II can be activated with ethanol according to the ethanol activation treatment as described in Presicce and Yang, *Mol. Reprod. Dev.*, 37:61-68 (1994); and Bordignon & Smith, *Mol. Reprod. Dev.*, 49:29-36 (1998). Exposure of calcium to the oocyte also occurs through electrical stimulation. The electrical stimulation allows increasing levels of calcium to enter the oocyte.

Oocytes can be obtained from a donor animal during that animal's reproductive cycle. For example, oocytes can be aspirated from follicles of ovaries at given times during the reproductive cycle (exogenous hormone-stimulated or non-stimulated). Also at given times following ovulation, a significant percentage of the oocytes, for example, are in telophase. Additionally, oocytes can be obtained and then induced to mature in vitro to arrested metaphase II stage. Arrested metaphase II oocytes, produced in vivo or in vitro, can then be induced in vitro to enter telophase. Thus, oocytes in telophase can readily be obtained for use in the present invention. In particular, oocytes can be collected from a female animal following super ovulations. Oocytes can be recovered surgically by flushing the oocytes from the oviduct of a female donor. Methods of inducing super ovulations in, for example, goats and the collection of the oocytes are described herein.

As described above, the enucleated oocyte is combined with the nucleus of the donor cell. The donor cell can be active or inactive. An activated (e.g., non-quiescent) donor cell is a cell that is in actively dividing (e.g., not in a resting stage, $G_1$ of mitosis). In particular, an activated donor cell is one that is engaged in the mitotic cell cycle, such as $G_1$ phase, S phase or $G_2/M$ phase. The mitotic cell cycle has the following phases, $G_1$, S, $G_2$ and M. The $G_2/M$ phase refers to the transitional phase between the $G_2$ phase and M phase. The commitment event in the cell cycle, called START (or restriction point), takes place during the $G_1$ phase. "START" as used herein refers to late $G_1$ stage of the cell cycle prior to the commitment of a cell proceeding through the cell cycle. The decision as to whether the cell will undergo another cell cycle is made at START. Once the cell has passed through START, it passes through the remainder of the $G_1$ phase (i.e., the pre-DNA synthesis stage). The S phase is the DNA synthesis stage, which is followed by the $G_2$ phase, the stage between synthesis and mitosis. Mitosis takes place during the M phase. If prior to START, the cell does not undergo another cell cycle, the cell becomes arrested. In addition, a cell can be induced to exit the cell cycle and become quiescent or inactive. A "quiescent" or "inactive" cell, is referred to as a cell in $G_0$ phase.

In one embodiment, the donor cell and oocyte can be "synchronous" with respect to the cell cycle. In this case, synchronization refers to cells that are in the same stage of cell division (e.g., in an active state). The meiotic cell stage of the activated oocytes correlates to the mitotic stage of the cell cycle of the activated donor cell. For example, an oocyte in telophase II fused with the genome of a donor cell in the $G_1$ stage before completion of the enucleation process provides a synchronization between the oocyte and the donor nuclei.

It is preferable that the donor cells also be in the same stage of cell division. Using donor cells at certain phases of the cell cycle, for example, $G_1$ phase, allows for synchronization of the donor cells. One can synchronize the donor cells and put them in the same stage by depriving (e.g., reducing) the donor cells of a sufficient amount of nutrients in the media that allows them to divide. Once the donor cells have stopped dividing, then the donor cells are exposed to media (serum) containing a sufficient amount of nutrients to allow them to being dividing (e.g., mitosis). The donor cells begin mitosis substantially at the same time, and are therefore, synchronous. For example, the donor cells are deprived of a sufficient concentration of serum by placing the cells in 0.5% Fetal Bovine Serum (FBS) for about a week. Thereafter, the cells are placed in about 10% FBS and they will begin dividing at about the same time. They will enter the G1 phase about the same time, and are therefore, ready for the cloning process.

Methods of determining which phase of the cell cycle a cell is in are known to those skilled in the art, for example, U.S. Pat. No. 5,843,705 to DiTiullio et al., Campbell, K. H. S., et al., *Embryo Transfer Newsletter*, vol. 14(1):12-16 (1996), Campbell, K. H. S., et al., *Nature*, 380:64-66 (1996), Cibelli, J. B., et al., *Science*, 280:1256-1258 (1998), Yong, Z. and L. Yuqiang, *Biol. of Reprod.*, 58:266-269 (1998) and Wilmut, I., et al., *Nature*, 385:810-813 (1997). For example, as described below in the Examples, various markers are present at different stages of the cell cycle. Such markers can include cyclines D 1, 2, 3 and proliferating cell nuclear antigen (PCNA) for $G_1$, and BrDu to detect DNA synthetic activity. In addition, cells can be induced to enter the $G_0$ stage by culturing the cells on a serum-deprived medium. Alternatively, cells in $G_0$ stage can be induced to enter into the cell cycle, that is, at $G_1$ stage by serum activation (e.g., exposing the cells to serum after the cells have been deprived of a certain amount of serum).

The donor cell can be any type of cell that contains a genome or genetic material (e.g., nucleic acid), such as a somatic cell, germ cell or a stem cell. The term "somatic cell" as used herein refers to a differentiated cell. The cell can be a somatic cell or a cell that is committed to a somatic cell lineage. Alternatively, any of the methods described herein can utilize a diploid stem cell that gives rise to a germ cell in order to supply the genome for producing a nuclear transfer embryo. The somatic cell can originate from an animal or from a cell and/or tissue culture system. If taken from an animal, the animal can be at any stage of development, for example, an embryo, a fetus or an adult. Additionally, the present invention can utilize embryonic somatic cells. Embryonic cells can include embryonic stem cells as well as embryonic cells committed to a somatic cell lineage. Such cells can be obtained from the endoderm, mesoderm or ectoderm of the embryo. Embryonic cells committed to a somatic cell lineage refer to cells isolated on or after approximately day ten of embryogenesis. However, cells can be obtained prior to day ten of embryogenesis. If a cell line is used as a source for a chromosomal genome, then primary cells are preferred. The term "primary cell line" as used herein includes primary cells as well as primary derived cell lines.

Suitable somatic cells include fibroblasts (for example, primary fibroblasts), epithelial cells, muscle cells, cumulous cells, neural cells, and mammary cells. Other suitable cells include hepatocytes and pancreatic islets.

The genome of the somatic cell can be the naturally occurring genome, for example, for the production of cloned animals, or the genome can be genetically altered to comprise a transgenic sequence, for example, for the production of transgenic cloned animals, as further described herein.

Somatic cells can be obtained by, for example, disassociation of tissue by mechanical (e.g., chopping, mincing) or enzymatic means (e.g., trypsinization) to obtain a cell suspension followed by culturing the cells until a confluent monolayer is obtained. The somatic cells can then be harvested and prepared for cryopreservation, or maintained as a stalk culture. The isolation of somatic cells, for example, fibroblasts, is described herein.

The nucleus of the donor cell is introduced before or upon exposure to the chemical or condition used to induce enucleation, or during any time prior cessation of protrusion of the second polar body containing essentially all of the endogenous chromatin. The donor nucleus and the enucleating oocyte can be combined in variety of ways to form the nuclear transfer embryo. For example, genome of a donor cell can be injected into the activated oocyte by employing a microinjector (i.e., micropipette or needle). The nuclear genome of the donor cell, for example, a somatic cell, is extracted using a micropipette or needle. Once extracted, the donor's nuclear genome can then be placed into the activated oocyte by inserting the micropipette, or needle, into the oocyte and releasing the nuclear genome of the donor's cell. See, for example, McGrath, J. and D. Solter, *Science,* 226:1317-1319 (1984), the teachings of which are incorporated by reference in their entirety.

Alternatively, the genome of a donor cell can be combined with an oocyte by fusion; e.g., electrofusion, viral fusion, liposomal fusion, biochemical reagent fusion (e.g., phytohemaglutinin (PHA) protein), or chemical fusion (e.g., polyethylene glycol (PEG) or ethanol). The nucleus of the donor cell can be deposited within the zona pelliduca which contains the oocyte. The steps of fusing the nucleus with the oocyte can then be performed by applying an electric field which will also result in a second activation of the oocyte. Anaphase II and/or Telophase II oocytes (e.g., oocyte having an extruding second polar body) used are already activated, hence any activation subsequent to or simultaneous with the introduction of genome from a somatic cell would be considered a second activation event. With respect to electrofusion, chambers, such as the BTX® 200 Embryomanipulation System for carrying out electrofusion are commercially available from for example BTX®, San Diego. The combination of the genome of the donor cell with the oocyte results in a nuclear transfer embryo.

A nuclear transfer embryo of the present invention is then transferred into a recipient animal female and allowed to develop or gestate into a cloned or transgenic animal. Conditions suitable for gestation are those conditions that allow for the embryo to develop and mature into a fetus, and eventually into a live animal. Such conditions are known in the art. For example, the nuclear transfer embryo can be transferred via the fimbria into the oviductal lumen of each recipient animal female. In addition, methods of transferring an embryo to a recipient known to those skilled in the art and are described in Ebert et al, *Bio/Technology,* 12:699 (1994). The nuclear transfer embryo can be maintained in a culture system until at least first cleavage (2-cell stage) up to the blastocyst stage, preferably the embryos are transferred at the 2-cell or 4-cell stage. Various culture media for embryo development are known to those skilled in the art. For example, the nuclear transfer embryo can be co-cultured with oviductal epithelial cell monolayer derived from the type of animal to be provided by the practitioner.

The present invention encompasses the cloning of a variety of animals. These animals include, for example, human or nonhuman mammals, (e.g., canines, felines, murine species (e.g., mice, rats), and ruminants (e.g., cows, sheep, goats, camels, pigs, oxen, horses, llamas)). In particular, goats of Swiss origin, for example, the Alpine, Saanen and Toggenburg bread goats can be used. The donor cell and the oocyte are preferably from the same species, and once combined, an animal of the same species is impregnated with embryo.

"Cloning an animal" refers to producing an animal that develops from an oocyte containing genetic information or the nucleic acid sequence of another animal, the animal being cloned. The cloned animal has substantially the same or identical genetic information as that of the animal being cloned. "Cloning" also refers to cloning a cell, which includes producing an oocyte containing genetic information or the nucleic acid sequence of another animal. The resulting oocyte having the donor genome is referred to herein as a "nuclear transfer embryo."

The present invention also relates to methods for generating transgenic animals. A transgenic animal is an animal that has been produced from a genome from a donor cell that has been genetically altered, for example, to produce a particular protein (a desired protein). Methods for introducing DNA constructs into the germ line of an animal to make a transgenic animal are known in the art. For example, one or several copies of the construct can be incorporated into the genome of a animal embryo by standard transgenic techniques.

Embryonal target cells at various developmental stages can be used to introduce transgenes. A transgene is a gene that produces the desired protein and is eventually incorporated into the genome of the activated oocyte. Different methods are used depending upon the stage of development of the embryonal target cell. The specific lines of any animal used to practice this invention are selected for general good health, good embryo yields, good pronuclear visibility in the embryo, and good reproductive fitness. In addition, the haplotype is a significant factor.

Genetically engineered donor cells for use in the instant invention can be obtained from a cell line into which a nucleic acid of interest, for example, a nucleic acid which encodes a protein, has been introduced.

A construct can be introduced into a cell via conventional transformation or transfection techniques. As used herein, the terms "transfection" and "transformation" include a variety of techniques for introducing a transgenic sequence into a host cell, including calcium phosphate or calcium chloride co-precipitation, DEAE dextrane-mediated transfection, lipofection, or electroporation. In addition, biological vectors, for example, viral vectors can be used as described below. Samples of methods for transforming or transfecting host cells can be found in Sambrook et al., *Molecular Cloning: A Laboratory Manual InSecond Edition, Cold Spring Harbor Laboratory*, (Cold Spring Harbor Laboratory Press, Cold Spring Harbor, N.Y. 1989). Two useful and practical approaches for introducing genetic material into a cell are electroporation and lipofection.

The DNA construct can be stably introduced into a donor cell line by electroporation using the following protocol: donor cells, for example, embryonic fibroblasts, are resuspended in phosphate buffer saline (PBS) at about $4 \times 10^6$ cells per mL. Fifty micrograms of linearized DNA is added to the 0.5 mL cell suspension, and the suspension is placed in a 0.4 cm electrode gap cuvette. Electroporation is performed using a BioRad Gene Pulser (Bio Rad) electroporator with a 330 volt pulse at 25 mA, 1000 microFarad and infinite resistance. If the DNA construct contains a neomyocin resistance gene for selection, neomyocin resistant clones are selected following incubation where 350 mg/mL of G418 (GIBCO BRL) for fifteen days.

The DNA construct can be stably introduced into a donor somatic cell line by lipofection using a protocol such as the following: about $2 \times 10^5$ cells are plated into a 3.5 cm well and transfected with 2 mg of linearized DNA using LipfectAMINE® (GIBCO BRL). Forty-eight hours after transfection, the cells are split 1:1000 and 1:5000 and if the DNA construct contains a neomyocin resistance gene for selection, G418 is added to a final concentration of 0.35 mg/mL. Neomyocin resistant clones are isolated and expanded for cyropreservation as well as nuclear transfer.

It is often desirable to express a protein, for example, a heterologous protein, in a specific tissue or fluid, for example, the milk of a transgenic animal. A heterologous protein is a protein that is not naturally made by the cloned species (e.g., a protein that is derived from a different species than the species being cloned). The heterologous protein can be recovered from the tissue or fluid in which it is expressed. For example, it is often desirable to express the heterologous protein in milk. Methods for producing a heterologous protein under the control of a milk-specific promoter is described below. In addition, other tissue-specific promoters, as well as, other regulatory elements, for example, signal sequences and sequences which enhance secretion of non-secreted proteins, are described below. The transgenic product (e.g., a heterologous protein) can be expressed, and therefore, recovered in various tissue, cells or bodily secretions of the transgenic animals. Examples of such tissue, cells or secretions are blood, urine, hair, skin, mammary gland, muscle, or viscera (or a tissue component thereof) including, but not limited to, brain, heart, lung, kidney, pancreas, gall bladder, liver, stomach, eye, colon, small intestine, bladder, uterus and testes. Recovery of a transgenic product from these tissues are well known to those skilled in the art, see, for example, Ausubel, F. M., et al., (eds), *Current Protocols in Molecular Biology*, vol. 2, ch. 10 (1991).

Useful transcriptional promoters are those promoters that are preferentially activated in mammary epithelial cells, including promoters that control the genes encoding protein such as caseins, β-lactoglobulin (Clark et al., *Bio/Technology*, 7:487-492 (1989)), whey acid protein (Gordon et al., *Bio/Technology*, 5:1183-1187 (1987)), and lactalbumin (Soulier et al., *Febs Letts.*, 297:13 (1992)). Casein promoters can be derived from the alpha, beta, gamma, or kappa casein genes of any animal species; a preferred promoter is derived from the goat β-casein gene (Ditullio, *Bio/Technology*, 10:74-77 (1992)). Milk specific protein promoter or the promoters that are specifically activated in mammary tissue can be derived from cDNA or genomic sequences.

DNA sequence information is available for the mammary gland's specific genes listed above, in at least one, and often in several organisms. See, for example, Richards et al., *J. Biol. Chem.*, 256:526-532 (1981) (α-Lactalbumin rat); Campbel et al., *Nucleic Acids Res.*, 12:8685-8697 (1984) (rat WAP); Jones et al., *J. Biol. Chem.*, 260:7042-7050 (1985) (rat β-Casein); Yu-Lee and Rosen, *J. Biol. Chem.*, 258:10794-10804 (1983) (rat α-Casein); Hall, *Bio. Chem. J*, 242:735-742 (1987); (α-Lactalbumin human); Stewart, *Nucleic Acids Res.*, 12:389 (1984) (Bovine α S1 and κ1 Casein, cDNAs); Gorodetsky et al., *Gene*, 66:87-96 (1988) (Bovine β-Casein); Alexander et al., *Eur. J. Biochem.*, 178:395-401 (1988) (Bovine and κ-Casein); Brignon et al., *Febs Let.*, 188:48-55 (1977) (Bovine α S2 Casein); Gamieson et al., *Gene*, 61:85-90 (1987); Ivanov et al., *Biol. Chem. Hopp-Seylar*, 369:425-429 (1988); Alexander et al., *Nucleic Acid Res.*, 17:6739 (1989) (Bovine β-Lactoglobulin); Vilotte et al., *Biochimie*, 69:609-620 (1987) (Bovine α-Lactalbumin).

The structure and function of the various milk protein genes are reviewed by Mercier & Vilotte, *J. Dairy Sci.*, 76:3079-3098 (1993). If additional flanking sequences are useful in optimizing expression of the heterologous protein, such sequences can be cloned using the existing sequences as probes. Mammary gland specific regulatory sequences from different organisms can be obtained by screening libraries from such organisms using known cognate nucleotide sequences, or antibodies to cognate proteins as probes.

Useful signal sequences such as milk specific signal sequences or other signal sequences which result in the secretion of eukaryotic or prokaryotic proteins can be used. Preferably, the signal sequence is selected from milk specific signal sequences, that is, it is from a gene which encodes a product secreted into milk. Most preferably, the milk specific signal sequence is related to the milk specific promoter used in the construct. The size of the signal sequence is not critical. All that is required is that the sequence be of a sufficient size to effect secretion of the desired recombinant protein, for example, in the mammary tissue. For example, signal sequences from genes coding for caseins, for example, α, β, γ or κ caseins and the like can be used. A preferred signal sequence is the goat β-casein signal sequence. Signal sequences from other secreted proteins, for example, proteins secreted by kidney cells, pancreatic cells, or liver cells, can also be used. Preferably, the signal sequence results in the secretion of proteins into, for example, urine or blood.

A non-secreted protein can also be modified in such a manner that it is secreted such as by inclusion in the protein to be secreted all or part of the coding sequence of a protein which is normally secreted. Preferably, the entire sequence of the protein which is normally secreted is not included in the sequence of the protein but rather only a sufficient portion of the amino terminal end of the protein which is normally secreted to result in secretion of the protein. For example, a portion which is not normally secreted is fused (usually at its amino terminal end) to an amino terminal portion of the protein which is normally secreted.

In one aspect, the protein which is normally secreted is a protein which is normally secreted in milk. Such proteins include proteins secreted by mammary epithelial cells, milk proteins such as caseins, β-lactoglobulin, whey acid protein, and lactalbumin. Casein proteins including, alpha, beta, gamma or kappa casein genes of any mammalian species. The preferred protein is P-casein, for example, goat β-casein. Sequences which encode the secreted protein can be derived from either cDNA or genomic sequences. Preferably, they are of genomic origin, and include one or more introns.

Other tissue specific promoters which provide expression in a particular tissue can be used. Tissue specific promoters are promoters which are expressed more strongly in a particular tissue than in others. Tissue specific promoters are often expressed exclusively in the specific tissue.

Tissue specific promoters which can be used include: a neural-specific promoter, for example, nestin, Wnt-1, Pax-1, Engrailed-1, Engrailed-2, Sonic-hedgehog: a liver specific promoter, for example, albumin, alpha-1, antitrypsin; a muscle-specific promoter, for example, myogenin, actin, MyoD, myosin; an oocyte specific promoter, for example, ZP1, ZP2, ZP3; a testus specific promoter, for example, protamine, fertilin, synaptonemal complex protein-1; a blood specific promoter, for example, globulin, GATA-1, porphobilinogen deaminase; a lung specific promoter, for example, surfactin protein C; a skin or wool specific promoter, for example, keratin, elastin; endothelium-specific promoter, for example, TIE-1, TIE-2; and a bone specific promoter, for example, BMP. In addition, general promoters can be used for expression in several tissues. Examples of general promoters, include β-actin, ROSA-21, PGK, FOS, c-myc, Jun-A, and Jun-B.

A cassette which encodes a heterologous protein can be assembled as a construct which includes a promoter for a specific tissue, for example, for mammary epithelial cells, a casein promoter. The construct can also include a 3' untranslated region downstream of the DNA sequence coding for the non-secreted proteins. Such regions can stabilize the RNA transcript of the expression system and thus increase the yield of desired protein from the expression system. Among the 3' untranslated regions useful in the constructs for use in the invention are sequences that provide a polyA signal. Such sequences can be derived, for example, from the SV40 small t antigen, the casein 3' untranslated region or other 3' untranslated sequences well known in the art. In one aspect, the 3' untranslated region is derived from a milk specific protein. The length of the 3' untranslated region is not critical but the stabilizing effect of its polyA transcript appears imported in stabilizing the RNA of the expression sequence.

Optionally, the construct can include a 5' untranslated region between the promoter and the DNA sequence encoding the signal sequence. Such untranslated regions can be from the same control region as that from which the promoter is taken or can be from a different gene, for example, they can be derived from other synthetic, semisynthetic or natural sources. Again, there specific length is not critical, however, they appear to be useful in improving the level of expression.

The construct can also include about 10%, 20%, 30% or more of the N-terminal coding region of a gene preferentially expressed in mammary epithelial cells. For example, the N-terminal coding region can correspond to the promoter used, for example, a goat β-casein N-terminal coding region.

The construct can be prepared using methods known to those skilled in the art. The construct can be prepared as part of a larger plasmid. Such preparation allows the cloning and selection of the correct constructions in an efficient manner. The construct can be located between convenient restrictions sites on the plasmid so that they can be easily isolated from the remaining plasmid sequences for incorporation into the desired animal.

Transgenic sequences encoding heterologous proteins can be introduced into the germ line of an animal or can be transfected into a cell line to provide a source of genetically engineered donor cells as described above. The protein can be a complex or multimeric protein, for example, a homo-or hetromultimeric proteins. The protein can be a protein which is processed by removing the N-terminus, C-terminus or internal fragments. Even complex proteins can be expressed in active form. Protein encoding sequences which can be introduced into the genome of an animal, for example, goats, include glycoproteins, neuropeptides, immmunoglobulins, enzymes, peptides and hormones. The protein can be a naturally occurring protein or a recombinant protein for example, a fragment or fusion protein, (e.g., an immunoglobulin fusion protein or a mutien). The protein encoding nucleotide sequence can be human or non-human in origin. The heterologous protein can be a potential therapeutic or pharmaceutical agent such as, but not limited to, alpha-1 proteinase inhibitor, alpha-1 antitrypsin, alkaline phosphatase, angiogenin, antithrombin III, any of the blood clotting factors including Factor VIII, Factor IX, and Factor X chitinase, erythropoietin, extracellular superoxide dismutase, fibrinogen, glucocerebrosidas, glutamate decarboxylase, human growth factor, human serum albumin, immunoglobulin, insulin, myelin basic protein, proinsulin, prolactin, soluble CD 4 or a component or complex thereof, lactoferrin, lactoglobulin, lysozyme, lactalbumin, tissue plasminogen activator or a variant thereof immunoglobulin particularly preferred protein. Examples of immunoglobulins include IgA, IgG, IgE, IgM, chimeric antibodies, humanized antibodies, recombinant antibodies, single chain antibodies and anti-body protein fusions.

Nucleotide sequence information is available for several of the genes encoding the heterologous proteins listed above, in at least one, and often in several organisms. See, for example, Long et al., *Biochem.*, 23(21):4828-4837 (1984) (Alpha-1 antitrypsin); Mitchell et al., *Prot. Natl. Acad. Sci. USA*, 83:7182-7186 (1986) (Alkaline phosphatase); Schneider et al., *Embo J.*, 7(13): 4151-4156 (1988) (Angiogenin); Bock et al., *Biochem.*, 27 (16):6171-6178 (1988) (Antithrombin); Olds et al., *Br. J. Haematol.*, 78(3): 408-413 (1991) (Antithrombin III); Lyn et al., *Proc. Natl. Acad. Sci. USA*, 82(22): 7580-7584 (1985) (erythropoietin); U.S. Pat. No. 5,614,184 (erythropoietin) Horowtiz, et al., *Genomics*, 4(1):87-96 (1989) (Glucocerebrosidase); Kelly et al., *Ann. Hum. Genet.*, 56(3):255-265 (1992) (Glutamate decarboxylase); U.S. Pat. No. 5,707,828 (human serum albumin); U.S. Pat. No. 5,652, 352 (human serum albumin); Lawn et al., *Nucleic Acid Res.*, 9(22):6103-6114 (1981) (human serum albumin); Kamholz et al., *Prot. Matl. Acad. Sci. USA*, 83(13):4962-4966 (1986) (myelin basic protein); Hiraoka et al., *Mol. Cell Endocrinol.*, 75(1):71-80 (1991) (prolactin); U.S. Pat. No. 5,571,896 (lactoferrin); Pennica et al., *Nature*, 301(5897):214-221 (1983) (tissue plasminogen activator); Sarafanov et al., *Mol. Biol.*, 29: 161-165 (1995).

A transgenic protein can be produced in the transgenic cloned animal at relatively high concentrations and in large volumes, for example in milk, providing continuous high level output of normally processed protein that is easily harvested from a renewable resource. There are several different methods known in the art for isolation of proteins for milk.

Milk proteins usually are isolated by a combination of processes. Raw milk first is fractionated to remove fats, for example by skimming, centrifugation, sedimentation, (H. E. Swaisgood, Development in Dairy Chemistry, I: Chemistry of Milk Protein, Applied Science Publishers, NY 1982), acid precipitation (U.S. Pat. No. 4,644,056) or enzymatic coagulation with rennin or chymotrypsin (Swaisgood, ibid.). Next the major milk proteins can be fractionated into either a clear solution or a bulk precipitate from which this specific protein of interest can be readily purified.

French Patent No. 2487642 describes the isolation of milk proteins from skim milk or whey by performing ultra filtration in combination with exclusion chromatography or ion exchange chromatography. Whey is first produced by removing the casein by coagulation with rennet or lactic acid. U.S. Pat. No. 4,485,040 describes the isolation of an a-lactoglobulin-enriched product in the retentate from whey by two sequential ultra filtration steps. U.S. Pat. No. 4,644,056 provides a method for purifying immunoglobulin from milk or colostrum by acid precipitation at pH 4.0-5.5, is sequential cross-flow filtration first on a membrane with 0.1-1.2 mm pore size to clarify the product pool and then on a membrane with a separation limit of 5-80 kD to concentrate it. Similarly, U.S. Pat. No. 4,897,465 teaches the concentration and enrichment of a protein such as immunoglobulin from blood serum, egg yolks or whey by sequential ultra filtration on metallic oxide membranes with a pH shift. Filtration is carried out first at a pH below the isoelectric point (pI) of the selected protein to remove bulk contaminants from the protein retentate, in next adding pH above the pI of the selected protein to retain impurities and pass the selected protein to the permeate. A different filtration concentration method is taught by European Patent No. EP 467 482 B 1 in which defatted skim milk is reduced to pH 3-4, below the pI of the milk proteins, to solubilize both casein and whey proteins. Three successive rounds of ultra filtration are diafiltration and concentrate the proteins to form a retentate containing 15-20% solids of which 90% is protein. Alternatively, British Patent Application No. 2179947 discloses the isolation of lactoferrin from whey by ultra filtration to concentrate the sample, fall by week cation exchange chromatography at approximately a neutral pH. No measure of purity is reported in PCT Publication No. WO 95/22258, a protein such as lactoferrin is recovered from milk that has been adjusted to high ionic strength by the addition of concentrated salt, followed by cation exchange chromatography.

In all these methods, milk or a fraction thereof is first treated to remove fats, lipids, and other particular matter that would foul filtration membranes or chromatography medium. The initial fractions thus produce can consist of casein, whey, or total milk protein, from which the protein of interest is then isolated.

PCT Patent Publication No. WO 94/19935 discloses a method of isolating a biologically active protein from whole milk by stabilizing the solubility of total milk proteins with a positively charged agent such as arginine, imidazole or Bis-Tris. This treatment forms a clarified solution from which the protein can be isolated for example by filtration through membranes that otherwise would become clogged by precipitated proteins.

Methods for isolating a soluble milk component such as a peptide in its biologically active form from whole milk or a milk fraction by tangential flow filtration are known. Unlike previous isolation methods, this eliminates the need for a first fractionation of whole milk to remove fat micelles, thereby simplifying the process in avoiding losses of recovery of bioactivity. This method can be used in combination with additional purification steps to further remove contaminants and purify the product (e.g., the protein of interest).

The following examples are intended to be illustrative and not limiting in any way.

EXEMPLIFICATION

Example 1

Improved Method of Cloning through the Introduction of Donor Cell Nucleus Prior to Completion of Enucleation Process Progress has continued with experiments designed to compare in vitro development of control embryos (parthenotes) with that of reconstructed NT embryos prepared by conventional NT, telophase NT, IE and a novel simultaneous IE-NT paradigm (SIE/NT; see Table 1 below). As in all previous experiments, abattoir-sourced oocytes were obtained having been submitted to 26 h of maturation in ACM medi a @5%$CO_2$ in air. Oocytes were denuded (enzyme/vortex) and activated (5 µM ionomyciin for 5 min, +/−CHX). See Example 2 for detail on methods. IE was performed by treatment of oocytes with demecolcine (0.4 µg/ml) starting at 1.5 h and ending 5 h post-activation (p.a.) and nuclei were injected 1.5-3 h p.a. In the case of SIE/NT, donor karyoplasts (fibroblasts) were injected immediately prior to or immediately after activation. In vitro embryo development was evaluated over a period of 7 days.

SUMMARY of Bovine NT in Vitro Development

| GROUP | Total oocytes | Cleavage | Morula | Blastocyst | Fragmented |
| --- | --- | --- | --- | --- | --- |
| Control Parthnotes Zona-intact | 67 | 58% (39/67) | 13% (5/39) | 21% (8/39) | 28% |
| Control Parthnotes Zona-free | 30 | 86% (26/30) | NA | 8% (2/26) | 41% |
| Conventional MII Enucleation (CMII) | 23 | 35% (8/23) | 17% (4/23) | 9% (2/23) | 22% |
| Telophase Enucleation (TE) | 55 | 62% (34/55) | NA | 12% (4/34) | 26% |
| Induced Enucleation (IE) | 144 | 49% (71/144) | 17% (12/71) | 16% (11/71) | 20% |
| Simultaneous IE-NT (SIE/NT) | 145 | 54% (79/145) | NA | 25% (20/79) | 18% |

In summary, these data further confirm the comparative in vitro development potential of NT embryos produced by conventional, telophase and IE protocols. Moreover, the SIE/NT protocol appears to support the highest rate of blastocyst development when compared to the other methods. This observation is further supports the mechanism by which higher NT development rates can be obtained using the IE method. This is founded on the concept that IE affords spindle-associated enabling factors to compartmentalize within the enucleating cytoplast in a manner and timeframe so as to enhance cytoplasmic-nuclear synchronization and chromatin remodeling.

Example 2

Demecolcine-Induced Oocyte Enucleation for Somatic Cell Cloning: Coordination Between Cell Cycle Egress, Kinetics of Cortical Cytoskeletal Interactions, and Second Polar Body Extrusions Studies were designed to further explore the use of pharmacological agents to create developmentally competent enucleated mouse oocytes for animal cloning by somatic cell nuclear transfer. Metaphase-II oocytes from CF-1 and B6D2F1 strains were activated with ethanol and subsequently exposed to demecolcine at various times post-activation. Chromosome segregation, spindle dynamics and polar body (PB) extrusion were monitored by fluorescence microscopy using DNA, microtubule and microfilament selective probes. Exposure to demecolcine did not affect rates of oocyte activation induced by ethanol but did disrupt the coordination of cytokinesis and karyokinesis, suppressing the extent and completion of spindle rotation and second PB extrusion in a strain-dependent manner. Moreover, strain and treatment specific variations in the rate of oocyte enucleation were also detected. In particular, CF-1 oocytes were more efficiently enucleated relative to B6D2F1 and demecolcine treatments initiated early after activation resulted in higher enucleation rates than when treatment was delayed. The observed strain differences are possibly due to a combination of factors such as the time course of meiotic cell cycle progression after ethanol-activation, the degree of spindle rotation and the extent of second PB extrusion. These results suggest that developmentally competent cytoplasts can be produced by timely exposure of activated oocytes to agents that disrupt spindle microtubules.

In the present study, the temporal consequences of demecolcine-induced enucleation with reference to the cytoskeletal remodeling that occurs during early phases of oocyte activation in CF-1 and B6D2F1 mouse strains was investigated. In particular, manifestations of demecolcine treatment on spindle rotation/anchoring dynamics, and second PB formation and extrusion were investigated.

Materials and Methods

Collection of Mature Oocytes

Hybrid B6D2F1 (C57BL/6×DBA/2) and outbred CF-1 female mice, 8-12 weeks of age, were used as oocyte donors. Animal care and procedures were conducted according to protocols approved by the Tufts University Institutional Animal Care and Use Committee. Females were induced to superovulate by intraperitoneal injection of 5 1U of pregnant mare serum gonadotropin (PMSG, Calbiochem) followed 48 h later by 5 1U of human chorionic gonadotropin (hCG, Calbiochem). MII oocytes were collected from oviducts 16-17 h after hCG administration in Hepes-buffered KSOM (H-KSOM, Specialty Media). Cumulus cells were dispersed by incubation in 150 units/ml of bovine testicular hyaluronidase (Sigma) in H-KSOM at 37° C. for 5 min. Cumulus-free oocytes were then washed three times in fresh H-KSOM and immediately activated.

Oocyte Activation, Treatment and Culture

Oocytes were parthenogenetically activated by a 5-min exposure to freshly prepared 7% (v/v) ethanol in H-KSOM at 37° C. and then washed twice in H-KSOM. Removal of oocytes from ethanol was considered as time zero post-activation (p.a.). To monitor meiotic progression, activated control oocytes (EtOH groups) were cultured for up to 2 h and 15 min and fixed at 30 min intervals, starting 45 min p.a. Culture of activated oocytes was at 37° C. under 5% COZ in air in KSOM medium containing 1 mg/ml BSA and amino acids (16; Specialty Media).

Other activated oocytes were treated with the microtubule-destabilizing drug demecolcine (Sigma) at a concentration of 0.4 gg/ml in KSOM (Deme groups). These oocytes were cultured in the continued presence of demecolcine starting either immediately after activation (Deme 0 groups) or with a delay of 5, 10 or 15 min after their removal from ethanol (Deme 5, Deme 10 and Deme 15 groups, respectively). Demecolcine-treated oocytes were fixed at 30 min intervals, from 45 min to 135 min p.a., identical to control oocytes. To determine oocyte meiotic status at the onset of demecolcine treatments, some control activated B6D2F1 and CF-1 oocytes were fixed at the same time drug exposure was initiated in the treatment groups: 0, 5, 10 and 15 min p.a.

Fixation of Oocytes and Processing for Immunofluorescence Analysis

At defined time-points after activation, control and demecolcine-treated oocytes were fixed and extracted for 30 min at 37° C. in a microtubule stabilizing buffer containing 0.1 M PIPES, 5 mM $MgCl_2$, 2.5 mM EGTA, 3.7% formaldehyde, 0.1% Triton X-100, 1 g, M taxol, 0.01% aprotinin, 1 mM dithiothreitol (DTT) and 50% deuterium oxide. Fixed oocytes were stored until processing at 4 C. in a PBS blocking solution containing 1% BSA, 0.2% powdered milk, 2% normal goat serum, 0.1 M glycine, 0.2% sodium azide and 0.01% Triton X-100. Wickramasinghe D, et al., *Dev Biol* 152:62-74 (1992).

A triple labeling protocol was used for the detection of microtubules, microfilaments and chromatin by fluorescence microscopy. Oocytes were first incubated for 1 h at 37° C. in a mixture of mouse monoclonal anti a-tubulin and anti (3-tubulin antibodies (Sigma) at a 1:1000 final dilution. After several washes in 0.1% polyvinylpyrrolidone (PVP)/PBS at room temperature, oocytes were incubated at 37° C. in PBS blocking solution for 30 min and then in a 1:150 dilution of a donkey antimouse fluorescein-conjugated IgG (Jackson ImmunoResearch) for 45 min at 37° C. Oocytes were washed again several times in 0.1% PVP/PBS and incubated at 37° C. for 30 min in 10 units/ml of Texas Red-conjugated phalloidin (Molecular Probes) to stain actin filaments. Finally, after extensive washing in 0.1% PVP/PBS, oocytes were incubated at room temperature for 15 min in 10 µLg/ml Hoechst 33258 (Molecular Probes) and mounted in 50% glycerol/PBS containing 25 mg/ml sodium azide.

Labeled oocytes were examined using a Zeiss IM-35 inverted epi-fluorescence microscope fitted with filters selective for Hoechst, fluorescene and Texas Red and a 50 W mercury lamp. Selected images were acquired using a Photometrics Cool Snap CCD camera (Roper Scientific Inc., Trenton, N.J.) running on Metamorph software (version 5.0, Universal Imaging Corp., Downington, Pa.).

Statistical Analysis

All demecolcine treatments were repeated at least three times and approximately 50 oocytes were examined per treatment at each defined time-point. Data were analyzed by $x^2$ test or Fisher's exact test. A probability value of $P<0.05$ was considered to be statistically significant.

Results

To monitor the effects of demecolcine on the meiotic cell cycle progression after activation and determine its efficiency in inducing oocyte enucleation, ethanol-activated oocytes of the B6D2F1 and CF-1 mouse strains were cultured in the presence of drug and analyzed at selected timepoints for microtubule (MT), microfilaments and chromatin organization. Exposure to demecolcine was continuous for 30-135 min, from 0, 5, 10 or 15 min p.a. Control activated oocytes were cultured for the same period of time in the absence of demecolcine.

Ethanol Activation Rates are Not Affected by Demecolcine Treatment:

The effect of demecolcine on the meiotic spindle was evident 15 min after the onset of treatment, since spindles in treated oocytes were smaller and displayed a lower MT density compared to untreated control activated oocytes. Although MT density decreased with extended exposure to drug, spindle MTs did not disappear completely and even after 2 h of treatment a few short MTs were detected in the majority of the oocytes.

Figure 3A:
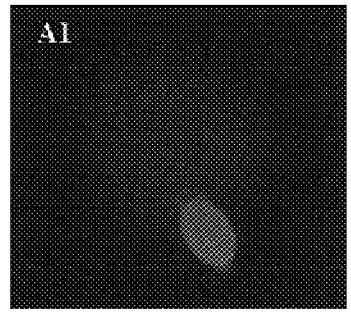
FIGS. 3A-3C are a series of photographs of ethanol-activated control and demecolcine-treated mouse oocytes fixed at 45 min post-activation and stained for microtubules (MTs), chromatin and microfilaments.
Figure 3A:
Figure 3B:
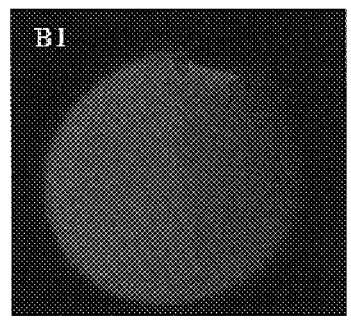
Figure 3B:
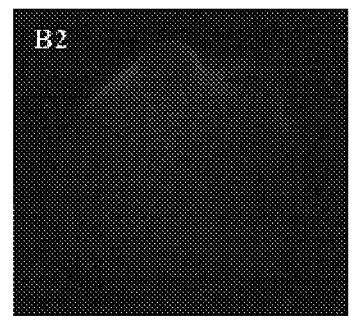
Figure 3C:
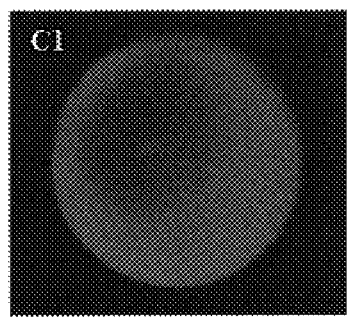
Figure 3C:
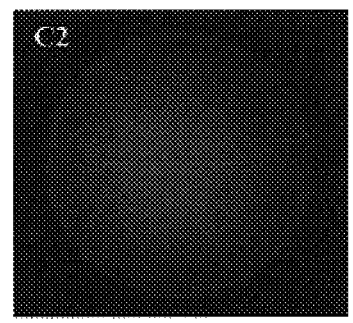
Figure 4A:
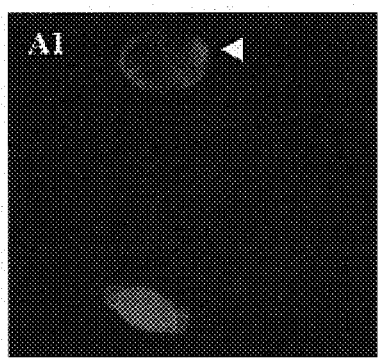
FIGS. 4A-4C are a series of photographs showing the progression of spindle rotation and initiation of second PB formation in ethanol activated control oocytes.
Figure 4A:
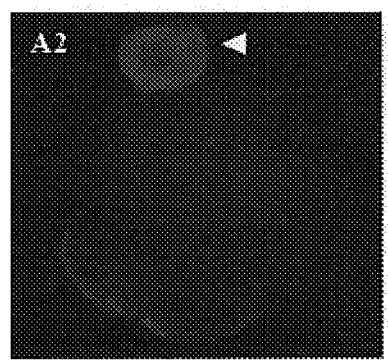
Figure 4B:
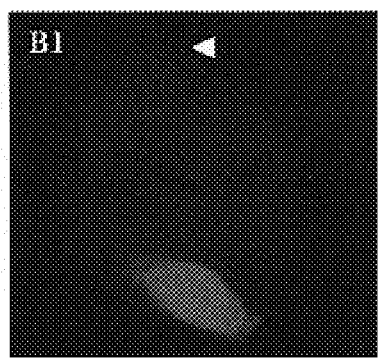
Figure 4B:
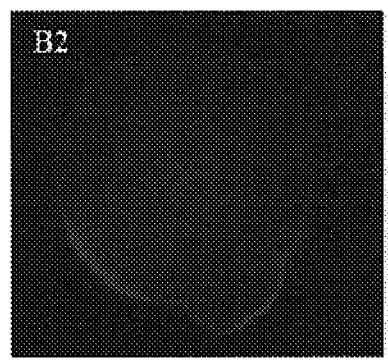
Figure 4C:
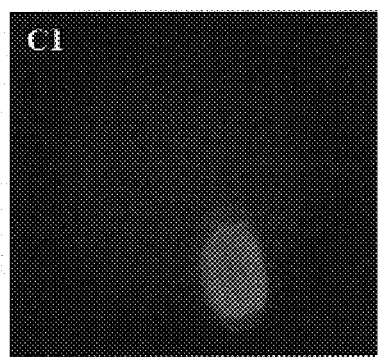
Figure 4C:
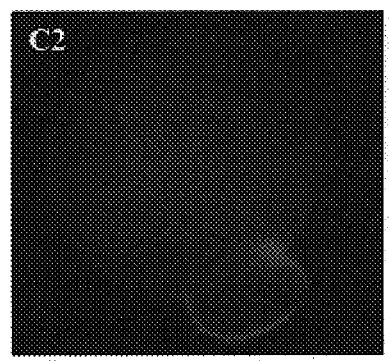
Figure 5A:
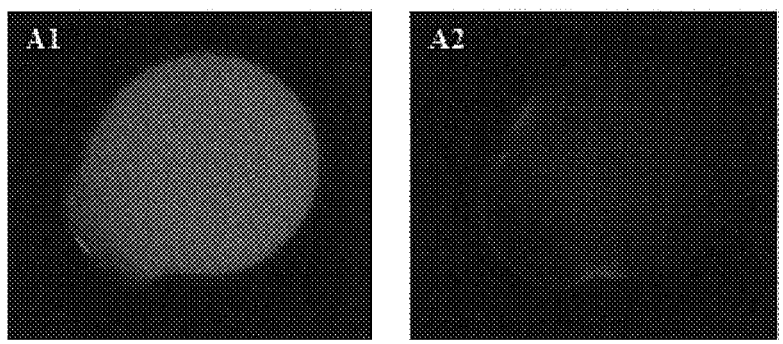
FIGS. 5A-5B are a series of micrographs showing activated demecolcine-treated mouse oocytes.
Figure 5B:
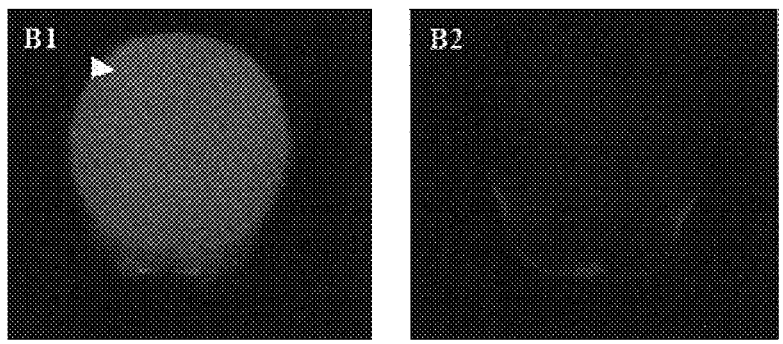

At 45 min p.a., 98% and 92.5% of the control activated B6D2F1 and CF-1 oocytes, respectively, had resumed meiosis as evidenced by chromatid segregation, spindle elongation and the presence of a large, actin-rich cortical protrusion or, in a few cases, a completely extruded second PB. These oocytes were considered activated (FIG. 3A). Similar rates of activation at 45 min p.a. (80-98%; Table 2) were observed in all groups of demecolcine-treated oocytes according to the same criteria, except that spindle elongation failed to occur. Although the extent of chromosome separation was reduced, due to spindle disruption, two distinct clusters of chromosomes were clearly visible in these treated activated oocytes indicating that an effective anaphase had occurred. The chromosomes were subcortical to the oocyte cortex, and usually connected by a spindle remnant that resembled a midbody (FIG. 3B). As in the control group, a small fraction of oocytes had already extruded a second PB. Interestingly, a single group of chromosomes and no detectable MTs were present in treated oocytes that failed to activate (FIG. 3C).

oolemma and gave rise to the second PB. Activated oocytes treated with demecolcine yielded two classes that displayed either a single (type A oocyte) or double (type B oocyte) cortical protrusions overlying the remnants of the spindle (FIG. 5). The two sets of chromosomes were closer to each other in type A oocytes than in type B oocytes, suggesting that the formation of one or two protrusions was probably dependent on the extent of meiotic cell cycle progression before spindle disruption. Consistent with this idea, type A oocytes were more frequently observed when demecolcine treatment started immediately or 5 min after activation (Deme 0 and Deme 5 groups, respectively) whereas the incidence of type B oocytes predominated when treatment was delayed for 10 or 15 min (Deme 10 and Deme 15 groups, respectively).

Initiation of spindle rotation occurred in all groups of demecolcine-treated oocytes, except for the group Deme 0 in the CF-1 strain, but at lower rates than in control activated oocytes (Table 3). Although only a few short spindle MTs were present in treated oocytes, orientation of spindle remnants and the two chromosomal sets relative to the plasma membrane was used as an indicator of spindle rotation. CF-1 oocytes treated with demecolcine consistently exhibited a comparatively low percentage of activated oocytes undergoing a partial or complete spindle rotation at all p.a. time points examined. Demecolcine also impaired spindle rotation in

TABLE 2

Activation rates of ethanol-activated oocytes (EtOH) and ethanol-activated oocytes treated with demecolcine (Deme) at different times (0-15 min) post-activation activated oocytes (n)

| Strain | Treatment | 45 min* | | 75 min* | | 105 min* | | 135 min* | |
|---|---|---|---|---|---|---|---|---|---|
| B6D2F1 | EtOH | 98 | (51) | 98.1 | (52) | 100 | (58) | 100 | (53) |
| | Deme 0 | 96 | (50) | 98 | (50) | 96 | (50) | 96 | (50) |
| | Deme 5 | 98 | (50) | 94 | (50) | 100 | (55) | 94.5 | (55) |
| | Deme 10 | 94 | (50) | 98.1 | (54) | 100 | (52) | 100 | (52) |
| | Deme 15 | 97.9 | (47) | 96 | (50) | 94 | (50) | 98 | (51) |
| CF-1 | EtOH | 92.5 | (67) | $97^a$ | (67) | $97.3^a$ | (74) | 100 | (48) |
| | Deme 0 | 92 | (50) | $98^a$ | (50) | $100^a$ | (50) | 95.9 | (49) |
| | Deme 5 | 82 | (50) | $76^b$ | (50) | $84.3^b$ | (51) | 98 | (51) |
| | Deme 10 | 80 | (50) | $84^b$ | (50) | $96^{a,b}$ | (50) | 94.7 | (57) |
| | Deme 15 | 94.2 | (52) | $100^a$ | (53) | $96.1^{a,b}$ | (51) | 95.9 | (49) |

*Time post-activation
$^{a,b}$Values with different superscripts within the same column and strain differ significantly ($P < 0.05$)

In the B6D2F1 strain, activation rates of demecolcine treated oocytes were equivalent to those of non-treated control oocytes at all time-points examined (Table 2). While rates of activation in some groups of CF-1 treated oocytes were lower than in the control group at 75 min and 105 min p.a., this effect was transitory and reversible since at 135 min after ethanol exposure activation rates were again equivalent among all groups. Therefore, normal rates of activation are obtained when activated oocytes are cultured in the continuous presence of demecolcine.

Effect of Demecolcine on Spindle Rotation in Activated Oocytes:

As noted by others, two cortical protrusions formed adjacent to each spindle pole shortly after activation in non-treated control oocytes. One protrusion then regressed as the spindle rotated towards the remaining protrusion, and assumed an orientation perpendicular to the plasma membrane (FIG. 4). Eventually this structure was constricted at the B6D2F1 oocytes at 45 min and 75 min p.a. when compared to the controls, but the effect was less pronounced than in CF-1 oocytes. However, a dramatic decrease in the percentage of B6D2F1 treated oocytes showing spindle rotation occurred in all treatment groups at 105 min and 135 min p.a., suggesting that spindle rotation was reversed with prolonged drug exposure. By 135 min p.a. oocytes showing complete spindle rotation were observed in only 0-9.6% of the CF-1 and B6D2F1 treated oocytes, compared to 100% in both control groups; and the lack of differences between demecolcine treatments further attested to the effectiveness of demecolcine on spindle rotation. In all, control and treated oocytes showing a completely rotated spindle at 135 min p.a. extrusion of the second PB had occurred. Together, these results indicate that continued exposure to demecolcine after oocyte activation inhibits spindle rotation independent of the time of initiation of the treatment and the strain of oocyte, although the kinetics of this inhibition varies between strains.

TABLE 3

Spindle rotation in ethanol-activated oocytes (EtOH) and ethanol-activated oocytes treated with demecolcine (Deme) at different times (0-15 min) post-activation activated oocytes with a partially or completely rotated spindle

| Strain | Treatment | 45 min | | 75 min* | | 105 min* | | 135 min* | |
|---|---|---|---|---|---|---|---|---|---|
| B6D2F1 | EtOH | 64.0$^a$ | (50) | 98.0$^a$ | (51) | 100$^a$ | (58) | 100$^a$ | (53) |
| | Deme 0 | 37.5$^b$ | (48) | 30.6$^b$ | (49) | 0$^b$ | (48) | 8.3$^b$ | (48) |
| | DemeS | 26.5$^b$ | (49) | 38.3$^b$ | (47) | 3.6$^b$ | (55) | 7.7$^b$ | (52) |
| | Deme 10 | 29.8$^b$ | (47) | 47.2$^b$ | (53) | 7.7$^b$ | (52) | 9.6$^b$ | (52) |
| | Deme 15 | 30.4$^b$ | (46) | 41.7$^b$ | (48) | 34.0$^c$ | (47) | 4.0$^b$ | (50) |
| CF-1 | EtOH | 58.1$^a$ | (62) | 84.6$^b$ | (65) | 94.4$^a$ | (72) | 100$^a$ | (48) |
| | Deme 0 | 0$^b$ | (46) | 0$^b$ | (49) | 0$^b$ | (50) | 0$^b$ | (47) |
| | Deme 5 | 4.4$^b$ | (45) | 2.6$^{b,c}$ | (38) | 2.3$^b$ | (43) | 4$^b$ | (50) |
| | Deme 10 | 2.5$^b$ | (40) | 2.4$^{b,c}$ | (42) | 4.2$^b$ | (48) | 1.8$^b$ | (54) |
| | Deme 15 | 6.1$^b$ | (49) | 13.2$^c$ | (53) | 6.1$^b$ | (49) | 2.1$^b$ | (47) |

*Time post-activation
$^{a\text{-}c}$Values with different superscripts within the same column and strain differ significantly (P < 0.05)

Figure 6A:
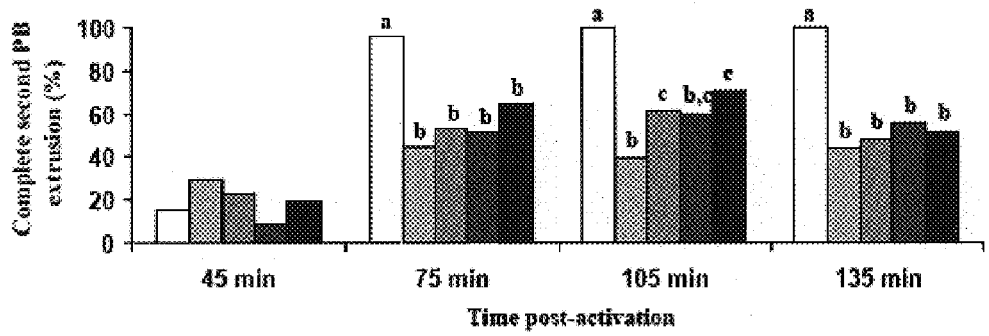
FIGS. 6A-6B are a series of histograms showing percent (%) of complete second PB extrusion at several times post-activation (45 min, 75 min, 105 min and 135 min) for untreated ethanol-activated oocytes (EtOH) or demecolcine (Deme)-treated activated oocytes at different times (0, 5, 10 and 15 min) post-activation.
Figure 6B:
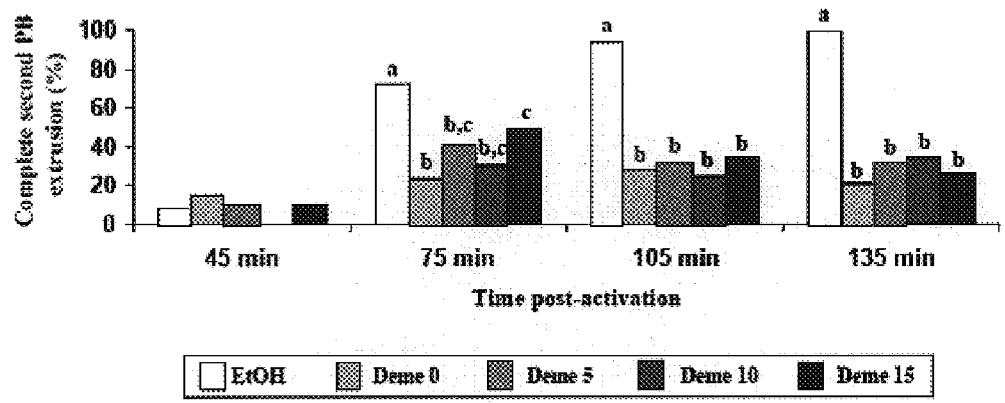

Complete Extrusion of the Second Polar Body is Inhibited in the Presence of Demecolcine:

While the onset of second PB formation was evident in all treated activated oocytes, forming one or two cortical protrusions overlying chromosomes, completion of second PB extrusion was impaired in the presence of demecolcine. By 45 min p.a., a small and similar percentage of activated control and treated oocytes displayed a completely extruded second PB (FIG. 6). Whereas the rates of PB extrusion in B6D2F1 and CF-1 control oocytes increased progressively with time, reaching 100% at 135 min p. a., complete PB extrusion in demecolcine-treated oocytes from both strains was significantly decreased, with rates ranging from 23.1% to 70.2% at the various time-points p.a. examined. Even though some differences were detected between treatments in both strains, a correlation between rates of second PB extrusion and the onset of demecolcine treatment could not be established. On the other hand, comparison of second PB extrusion rates in demecolcine-treated oocytes from both strains revealed significant differences between groups Deme 10 at 75 min p.a., between all treatment groups at 105 min p.a., and between groups Deme 0, Deme 10 and Deme 15 at 135 min p.a. These results suggest a strain-dependent effect of demecolcine on the suppression of second PB extrusion, being more pronounced in oocytes from the CF-1 strain.

Figure 7A:
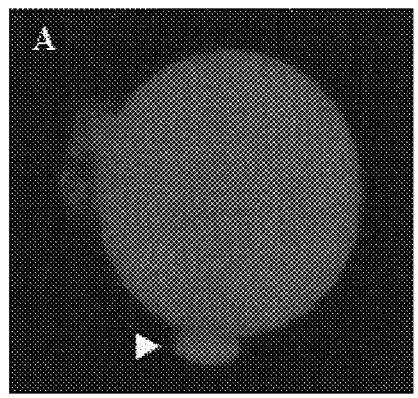
FIGS. 7A-7C are a set of micrographs showing demecolcine-treated oocyte.
Figure 7B:
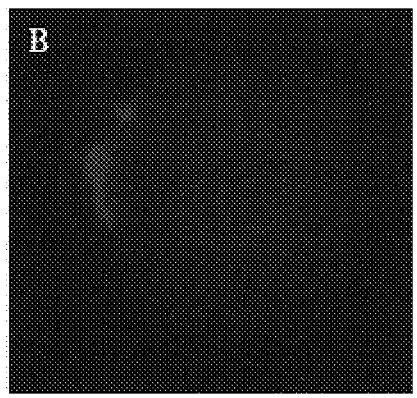
Figure 7C:
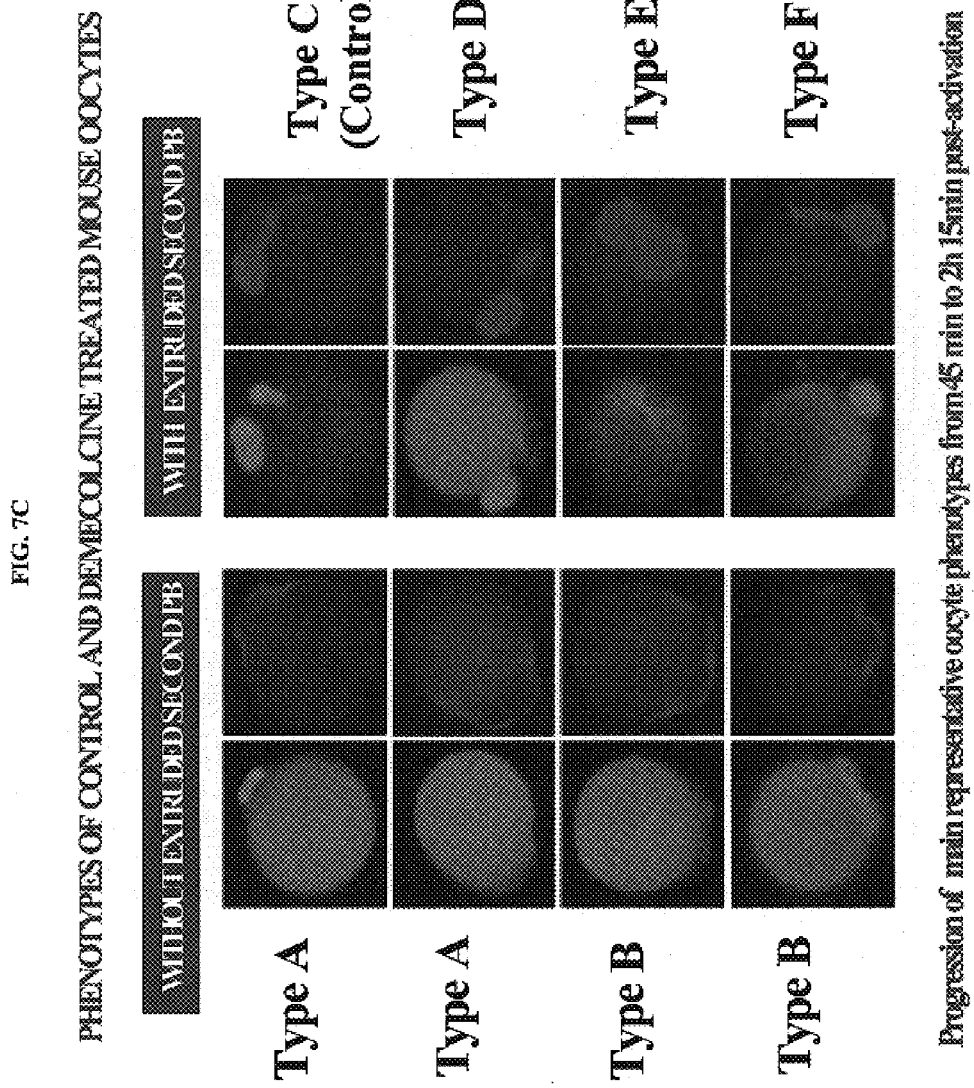

In those demecolcine-treated oocytes that failed to extrude a second PB, cortical protrusions enlarged over time and, in some oocytes, showed signs of constriction at the oolemma (FIG. 7). To determine whether PB extrusion was merely delayed in these oocytes, they were cultured for a longer period of time (4 h) before fixation and analysis. In most of the oocytes the cortical protrusion/s were reabsorbed while the formation of two pronuclei indicated that the cell cycle progressed to early interphase. As described infra, FIG. 7C shows oocytes (Types A and B) that have been exposed to demecolcine, and as a result completion of cytokinesis of the second PB was prevented. FIG. 7C also depicts oocytes (Type D, E and F) that have fully extruded second PB.

Figure 8A:
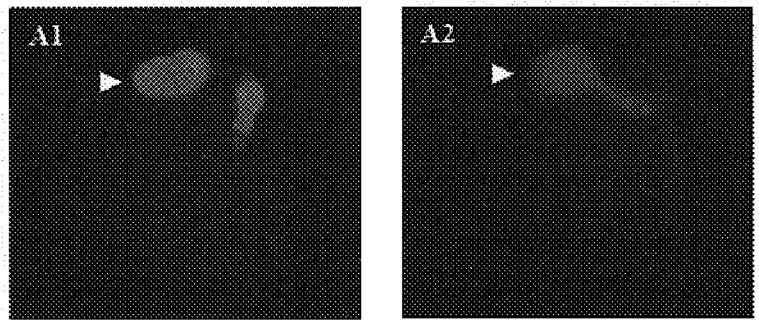
FIGS. 8A-8D are a series of photographs showing the phenotypes of activated control and demecolcine-treated oocytes that completed second PB extrusion. For each oocyte, microtubules (green) and chromatin (blue, H258) staining patterns are shown on the left (A1-D1), and microfilaments (red, rhodamine pholloidin) staining is shown on the right (A2-D2).
Figure 8B:
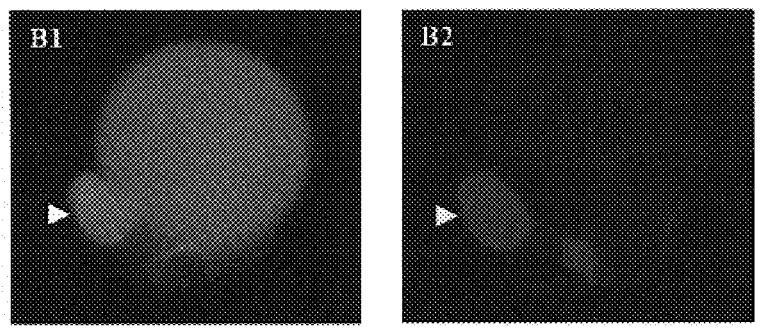
Figure 8C:
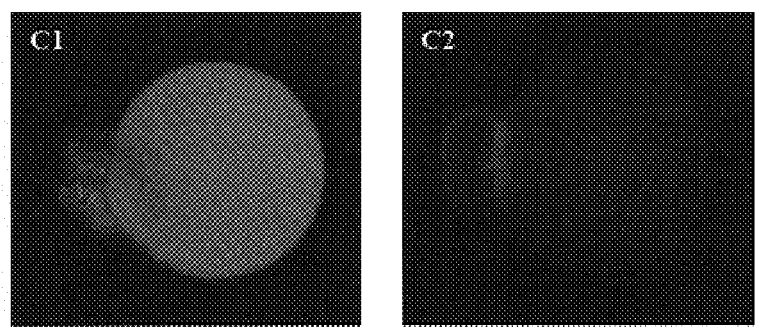
Figure 8D:
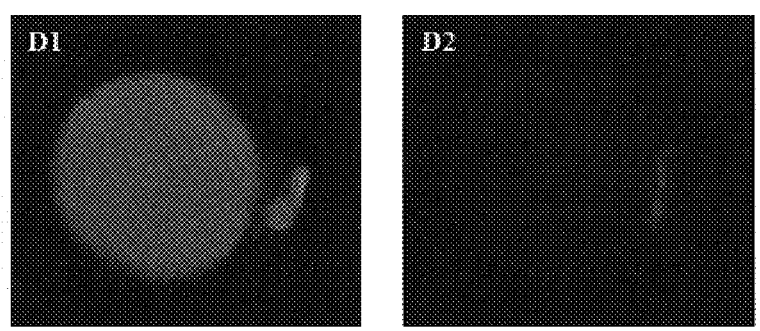

Characteristic Phenotypes are Observed in Activated Oocytes Treated with Demecolcine that Complete Second Polar Body Extrusion:

All control activated oocytes extruded a second PB containing half of the chromosomal complement and displayed a midbody perpendicular to the plasma membrane. This phenotype was classified as type C (FIG. 8A) and was also observed in a fraction of demecolcine-treated oocytes with completely extruded second PBs. However, midbodies in type C treated oocytes were narrower and shorter than in type C control activated oocytes, and were defined as midbody-like structures. Other treated oocytes that completed second B extrusion displayed characteristic phenotypes that were never detected in control activated oocytes. Type D oocytes (FIG. 8B) deployed one set of chromosomes in the oocyte cytoplasm and one set inside the extruded second PB, connected by a midbody-like structure as in type C oocytes. However, the midbody-like structure was oriented in parallel to the plasma membrane, indicating that spindle rotation had not occurred. Moreover, a prominent protuberance adjacent to the second PB was present in type D oocytes, probably due to the subcortical position of the chromosomal complement in the oocyte in the absence of spindle rotation. Other demecolcine-treated oocytes displayed two (Type E; FIG. 8C) or one (Type F; FIG. 8D) completely extruded second PBs that contained all chromosomes. Therefore, type E and F represent totally enucleated oocytes. As described infra, FIGS. 8C-8D show completed second PB formation. Rotation of the spindle had not occurred in these oocytes either, as evidenced by the parallel orientation of the remaining spindle MTs and the two sets of chromosomes inside the PB to the plasma membrane.

Figure 9:
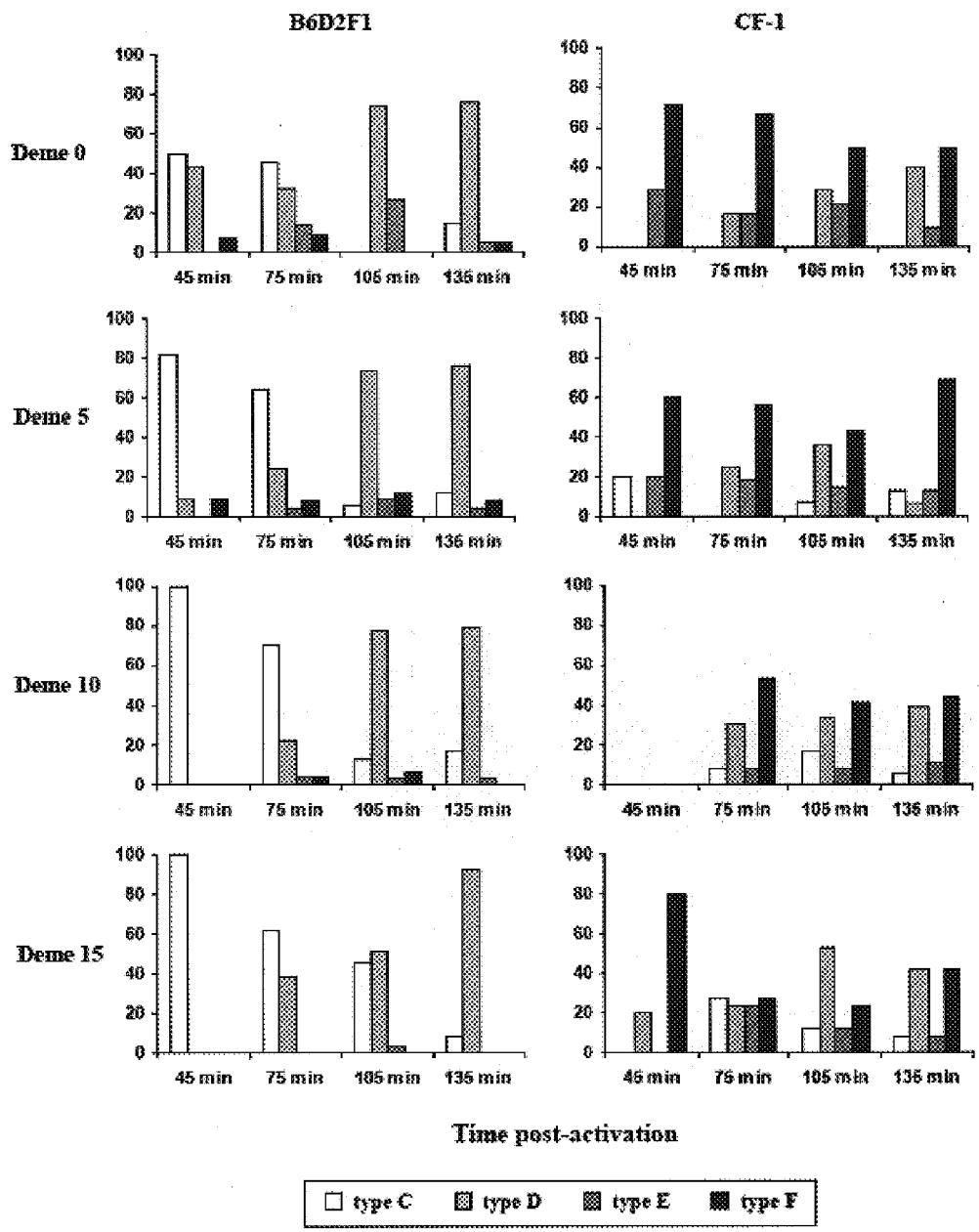
FIG. 9 is a series of histograms showing percent (%) of complete second PB extrusion at several times post-activation (45 min, 75 min, 105 min and 135 min) for various types of B6D2 μl and CF-1 strain oocytes (type C, type D, type E and type F) that were treated with demecolcine (Deme) at different times (0, 5, 10 and 15 min) post-activation.

The frequency of each of these phenotypes varied according to the onset of the demecolcine treatment with regards to activation, the duration of the treatment, and the strain of the oocyte, further indicating variability in the responsiveness of demecolcine (FIG. 9). In B6D2F1 oocytes, type C was the most frequent at 45 min and 75 min p.a. in all treatments, except for Deme 0 group in which it was detected at similar rates as type D. Prolonged exposure, independent of when treatment was initiated, caused a shift to type D phenotype, as seen by the high percentage of type D oocytes at 135 min p.a. in all treatments. CF-1 oocytes exhibited a strikingly different response. For all treatments, type F was the main phenotype in those oocytes that completed second PB extrusion by 45 min p.a. An increase in the frequency of type D oocytes was observed over time, and at 135 min p.a. type D and type F oocytes appeared at a similar frequency, except for the group Deme 5 in which most of the oocytes were still of type F.

Figures 10A, 10B:
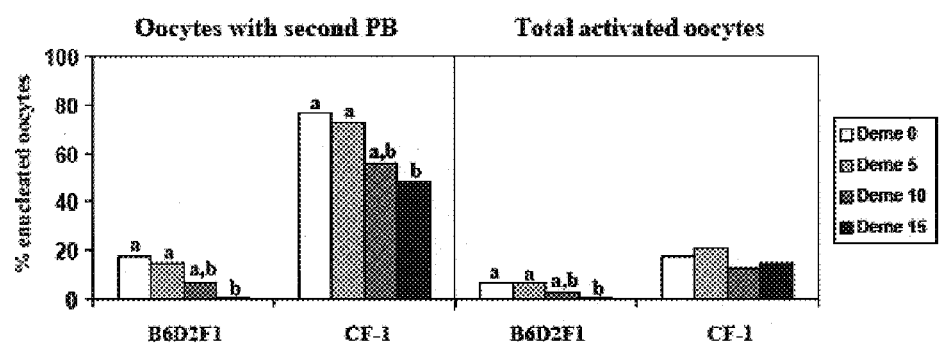
FIGS. 10A-10B are a set of histograms showing percent (%) of enucleation rates in ethanol-activated B6D2F1 and CF-1 mouse oocytes treated with demecolcine (Deme) at different times (0, 5, 10 and 15 min) post-activation (p.a.).

Treatment of Activated Oocytes with Demecolcine Induces Enucleation in a Strain-Dependent Manner:

According to the previous results, most CF-1 oocytes that completed extrusion of the second PB were enucleated as a result of demecolcine exposure, while the majority of B6D2F1 treated oocytes retained half of the chromosomal complement. This result is summarized in FIG. 10, which shows the combined results for all time-points examined of the total oocytes enucleated as a result of the various demecolcine treatments applied. Enucleation rates ranging from 48.3% to 76.7% were obtained in those CF-1 oocytes that completed second PB extrusion, and from 1% to 17.3% in the B6D2F1 strain (FIG. 10A). In the four treatments applied, the rates of enucleation were significantly higher in CF-1 than in B6D2 µl oocytes, suggesting that the efficiency of demecolcine in inducing oocyte enucleation is strain-dependent. Moreover, enucleation efficiency was also dependent on the time treatment was initiated p.a., as indicated by the higher enucleation rates obtained in both strains of oocytes when demecolcine treatment was initiated soon after activation rather than later.

Because of the low rates of complete PB extrusion in demecolcine-treated oocytes, when the total activated oocytes are considered there is a dramatic decrease in the rates of enucleation (FIG. 10B). Maximum enucleation rates of only 21% and 6.9% in CF-1 and in B6D2F1 oocytes, respectively, were obtained and again the enucleation efficiency in all four treatments was higher in CF-1 than in B6D2F1 oocytes. Although enucleation rates of the total activated oocytes were equivalent between treatments in CF-1 oocytes, some differences were detected between B6D2F1 oocytes subjected to different treatments. These differences indicated, again, that exposure to demecolcine early after activation results in higher rates of enucleation than when the treatment is delayed.

Meiotic Cell Cycle Progression After Activation is Strain-Dependent:

In order to determine if the different efficiency of demecolcine to induce enucleation in CF-1 and B6D2 µl oocytes could be related to variations in the oocyte meiotic progression after activation, some control activated oocytes were fixed at the same time-points p.a. when the demecolcine treatments were initiated. As demecolcine effects on the meiotic spindle are not immediate, the meiotic progression at 45 min p.a. was also recorded. Although the time course of activation was similar in oocytes from the two strains, the rate of cell cycle progression after the activation stimulus was slightly different (Table 4). Release from MR arrest and entry into anaphase followed a similar progression in the two groups of oocytes after ethanol exposure, but the anaphase-telophase transition proceeded faster in CF-1 oocytes. Thus, 2.6% and 4.4% of activated CF-1 oocytes were at telophase II 10 min and 15 min p.a., respectively, while all activated B6D2F1 oocytes remained at anaphase II. By 45 min p.a. 87.1% of activated CF-1 oocytes had entered telophase II, a value significantly higher than the 60% observed for activated B6D2F1 oocytes.

TABLE 4

Time course of activation rates and meiotic status of B6D2F1 and CF-1 oocytes after ethanol activation

| Strain | Time p.a.* | n | % activated oocytes | Meiotic status** |
|---|---|---|---|---|
| B6D2F1 | 0 min | 50 | 64.0 | 100% A |
| | 5 min | 49 | 57.1 | 100% A |
| | 10 min | 49 | 69.4 | 100% A |
| | 15 min | 52 | 84.6 | 100% A |
| | 45 min | 51 | 98.0 | 40% A, 60% T$^a$ |
| CF-1 | 0 min | 50 | 60.0 | 100% A |
| | 5 min | 50 | 74.0 | 100% A |
| | 10 min | 50 | 78.0 | 97.4% A, 2.6% T |
| | 15 min | 50 | 90.0 | 95.6% A, 4.4% T |
| | 45 min | 67 | 92.5 | 12.9% A, 87.1% T$^a$ |

*Removal from ethanol is considered as t = 0 min post-activation (p.a.)
**Only of activated oocytes A anaphase; T telophase
$^a$Values significantly different between the two strains (P < 0.05)

Discussion

The microtubule-destabilizing drug, demecolcine, was used to induce enucleation of pre-activated mouse oocytes of the B6D2F1 strain as a means to prepare competent cytoplasts for nuclear transfer procedures. Additionally, the data described herein shows the relationship between oocyte cell cycle control and the cytoskeleton during exit from meiotic metaphase (M-phase).

Resumption of meiosis after fertilization or artificial activation of M II-arrested oocytes is characterized by chromosome segregation to the spindle poles, elongation and rotation of the meiotic spindle, and extrusion of a second PB containing half of the chromosomal complement of the oocyte. M-phase exit is triggered by the inactivation of maturation-promoting factor (MPF) and it is now well established that cyclin B degradation, and thus MPF inactivation, requires an intact spindle. Consistent with this, MII oocytes treated with demecolcine or nocodazole prior to in vitro fertilization or parthenogenetic activation remain arrested in M-phase, despite the occurrence of a normal pattern of calcium oscillations. The exact mechanism by which the meiotic spindle mediates the transition from meiotic M-phase to embryonic interphase remains unclear. In the data described herein, oocytes activated with ethanol prior to demecolcine treatment exhibited activation rates comparable to activated control oocytes never exposed to demecolcine. Ethanol exposure induces an immediate increase in intracellular calcium and rapid progression into anaphase, as evidenced by the rapidity of meiotic cell cycle resumption in control activated oocytes from the two strains analyzed in this work. Because a delay exists between the onset of demecolcine application and detectable signs of spindle MT disruption, the acute effects of ethanol on cell cycle resumption are not impeded. In fact, as the results in control activated oocytes show, most oocytes (>_60%) exited M-phase and progressed to anaphase by the end of the 5 min ethanol exposure (0 min p.a.). Therefore, most of the oocytes were already at anaphase II or at the anaphase-telophase transition when the demecolcine treatment was applied. When demecolcine is applied after the activation stimulus, activation proceeds in the presence of the drug. However, at later stages there were clear consequences of demecolcine exposure that altered the relationship between karyokinesis and cytokinesis.

Also as shown herein, demecolcine binds tightly to tubulin dimers and prevents MT polymerization, resulting in the loss of dynamic spindle MTs in mitotic and meiotic cells. Immunofluorescence staining with antitubulin antibodies confirmed the time course and extent of spindle disruption by demecolcine and showed further that few short MTs remain in the majority of oocytes even after prolonged (2 h) drug exposure. The presence of these spindle remnants reflects differential stability of some MTs in the spindle, and likely correspond to interpolar MTs. Spindle disruption impaired the extent of chromatid segregation under these conditions. However, because oocytes were activated prior to demecolcine treatment, the observed variable degrees of chromosome segregation most likely result from the time of demecolcine administration, its uptake kinetics and variations in anaphase onset or duration. These results establish that cell cycle activation occurs prior to gross disruptions of spindle stability.

In early telophase, the meiotic spindle rotates from a parallel to a perpendicular orientation relative to the plasma membrane coincident with the initiation of second PB formation (see FIG. 8). Although the mechanism of spindle rotation is unclear, the presence of an actin-rich cortical domain overlying the spindle coupled with the inhibition of spindle rotation in both mouse and Xenopus oocytes treated with cytochalasin suggests that the interaction of spindle MTs with actin filaments of the cell cortex mediates spindle rotation and serves to coordinate karyokinesis and cytokinesis. Consistent with this, disruption of the spindle should also inhibit its rotation, as the results with demecolcine demonstrate. In fact, some demecolcine treated oocytes undergo some degree of spindle rotation, especially in the case of B6D2F1 eggs, but the process is completed in less than 10% of the oocytes. These observations suggest that spindle rotation is initiated before demecolcine induces depolymerization of the spindle MTs, which as a result perturbs interactions between MTs and cortical microfilaments and impairs further rotation of the spindle. Although suppression of spindle rotation occurred in both strains of oocytes examined, the percentage of oocytes with partially or completely rotated spindles at 45 and 75 min p.a. was higher in the B6D2F1 than in the CF-1 strain. This result indicates strain-dependent variation in the kinetics of inhibition of spindle rotation induced by demecolcine, that can not be related to interstrain differences in (a) the initiation and progression of spindle rotation and in (b) the rate of cell cycle progression (as detected in control activated oocytes from the two strains). Thus, these strain-dependent variations could be due to other factors associated with elongation and anchoring of the spindle such as centrosome positioning.

An additional effect of demecolcine was inhibition of second PB extrusion. The initial phase of PB formation, described as a "furrowing" of the plasma membrane in the region overlying the spindle, occurred in most treated oocytes, as evidenced by the formation of one or two actin-rich cortical protrusions. However, later "furrow constriction" and abscission was generally impaired in oocytes activated in the presence of demecolcine. Nocodazole or demecolcine treatment prior to furrowing and cleavage in sea urchin eggs has shown that MTs are required for furrow stimulation and the formation of the actomyosin contractile ring. But once furrowing has been stimulated, MTs are unnecessary. MTs are important for abscission, as depolymerization of the central spindle in late anaphase blocks the completion of cytokinesis. Several proteins necessary for cytokinesis have been localized to the central spindle and it has been suggested that MTs could serve as tracks along which these proteins and other components of the cell move into the cleavage furrow. Specifically, the presence of a functional midbody is required in mammalian cells to complete division. Formation of the midbody begins in anaphase, when MT bundles assemble in the central spindle, but functional midbody assembly also requires formation of new MTs nucleated by y tubulin centers during telophase. In view of this, suppression of new MT polymerization would be expected in demecolcine-treated oocytes and could underlie the inhibition of second PB extrusion. Interestingly, midbody-like structures were detected in some of the treated oocytes that completed second PB extrusion, and specifically in all type C and type D oocytes. As MTs that form the central spindle and the midbody are extremely stable, it is possible that some MT bundles could assemble in these oocytes before extensive MT depolymerization, forming a midbody-like structure that persisted. However, detection of these midbody-like structures in oocytes with a completely extruded second PB argues against the need of newly nucleated MTs for the completion of cytokinesis, unless this is not required for PB abscission or a different mechanism was used in these oocytes to complete division. In fact, second PB extrusion in type E and type F oocytes was completed in the absence of a midbody or a midbody-like structure. Spindle rotation had not occurred in these oocytes and the spindle remnants together with all chromosomes were extruded inside the second PB, leaving an enucleated oocyte. Interestingly, chemically enucleated mouse oocytes produced by a combined treatment with etoposide and cycloheximide also extrude PBs containing all oocyte chromosomes without involvement of the spindle. Completion of cytokinesis in the absence of MTs has also been reported in other studies and a midbodyindependent mechanism for cytokinesis has been proposed to exist in mammalian cells. Thus, it is also possible that in all or some of the demecolcine-treated oocytes that completed second PB extrusion this alternative mechanism was used due to the absence of a midbody or the presence of a non-functional midbody-like structure. The mechanism of PB extrusion and its dependence on midbody integrity will require further study.

Suppression of second PB extrusion in the presence of demecolcine was independent of the time of treatment but was dependent on the strain of the oocytes tested. In general, the incidence of second PB extrusion was lower in CF-1 than in B6D2F1 treated oocytes. Almost all B6D2F1 treated oocytes with an extruded second PB were of type C or type D and exhibited a midbodylike structure. On the other hand, as the results in control activated oocytes show, extrusion of the second PB seems to proceed somewhat faster in the B6D2F1 strain (see FIG. 6). Therefore, strain-specific variations in the time course of midbody formation and second PB extrusion can explain the observed differences between CF-1 and B6D2F1 treated oocytes.

Timely perturbation in spindle function during second PB extrusion also resulted in oocyte enucleation. Inhibition of spindle rotation and the extent of chromosome migration in the presence of demecolcine probably contributed to the expulsion of the entire chromosome complement inside one, or occasionally two, second PBs. As the results shows herein, the onset of the demecolcine treatment in relation to activation is key to achieving enucleation. Application of demecolcine immediately or a few minutes after ethanol exposure results in higher enucleation rates than application of the drug 15 min after activation, and this finding suggests that the extent of chromatid segregation is a key determinant of enucleation. In addition, a strain effect was also observed for enucleation efficiency, but the reasons for this are unclear. If the proximity of the two groups of chromosomes were decisive for enucleation, slower progression into telophase after activation would favor enucleation. However, a faster anaphase/telophase transition was observed in control activated oocytes of the CF-1 strain, with higher rates of enucleation in all demecolcine treatments, than of the B6D2F1 strain, with lower rates of enucleation. Thus, other parameters account for the strain-dependent efficiency of enucleation.

The majority of CF-1 oocytes treated with demecolcine that completed second PB extrusion were enucleated, and enucleation rates close to 80% were obtained. However, since many activated oocytes failed to complete second PB extrusion, the overall enucleation efficiency approximated 20%. Therefore, at least in the CF-1 strain, impairment of PB extrusion is a limitation to enucleation. Shorter treatments with demecolcine, that would allow MT regeneration by late telophase, can promote the completion of second PB extrusion. In fact, preliminary studies with oocytes exposed to demecolcine for only 15, 30 or 45 min resulted in slightly higher rates of second PB extrusion but the rates of oocyte enucleation were also reduced (unpublished results). As the effects of demecolcine on MT depolymerization and regeneration are not immediate with respect to time of application and removal, synchronization of treatment with oocyte cell cycle stage can be difficult to achieve. Possibly the use of other MT-disrupting drugs such as nocodazole, which have more rapid and reversible effects, provide better control over the integration of cytokinesis and karyokinesis.

Culture of activated mouse oocytes in the presence of demecolcine results in normal rates of oocyte activation and progressive cytoskeletal changes after activation. Disruption of spindle MTs by demecolcine impairs chromosome migration, suppresses spindle rotation, inhibits second PB extrusion, alters chromosome partitioning and thereby results in the generation of enucleated oocytes. Enucleation efficiency depends both on the onset of the demecolcine treatment in relation to oocyte activation and on the genetic background of the oocyte. This protocol can then be applied to prepare recipient cytoplasts in nuclear transfer procedures.

Example 3

Activated Bovine Cytoplasts Produced by Induced Enucleation Support Development of Nuclear Transfer Embryos In Vitro Poor efficiency of somatic cell NT has been associated with the preparation of developmentally competent enucleated cytoplasts. Induced enucleation (IE) of mouse oocytes has been shown to support enhanced term development of cloned mice. This study characterized the kinetics and phenotypic progression of bovine oocytes subjected to IE, and evaluated their developmental competence to support NT embryo development in vitro. In vitro matured (26 h) oocytes were denuded, activated (5 pM ionomycin, 5 min, then 10 μg/mL cycloheximide, 5 h) and cultured for up to 5 h post-activation (pa). Oocyte enucleation was induced by demecolcine (0.4 μg/ml, DM) exposure at 30, 60, 90 and 120 min post activation for various time periods (1 to 4.5 h). Activation rates and meiotic progression of control and DM treated oocytes (n=31-49/gp) was evaluated at 5 hpa by immunofluorescence microscopy (microtubule—Mab-FITC, microfilament—Texas red-phalloidin and chromatin-H33258). DM treatment at 30 min pa resulted in low activation rates (10-16%) whereas DM exposure at 1, 1.5 or 2 hpa resulted in higher (79-100%) oocytes activation rates. Onset and duration of DM treatment significantly altered IE rates, which varied from 60-91% at 5hpa. Maximum rates of IE were obtained when oocytes were exposed to DM between 1.5 and 5hpa (91% IE at 5hpa). DM treatments elicited a range of distinct oocyte spindle, chromatin, microfilament and PB phenotypes. Development of reconstructed IE embryos was evaluated by culture in vitro for 7 days. Mechanically isolated adult fibroblast nuclei were injected into IE cytoplasts between 1.5-3 hpa (n=106). Parthenogenetically activated and DM treated oocytes were cultured simultaneously for 7 days and served as controls. Control group cleavage and morula/blastocyst rates were 49% (23/47) and 30% (7/23) respectively, whereas IE group rates were 48% (51/106) and 27% (14/51) respectively. These results demonstrate that the IE method can be used to produce enucleated bovine cytoplasts and that IE cytoplasts are competent to support in vitro development. This technically simple approach provides a more efficient method to prepare competent cytoplasts for use in nuclear transfer procedures.

Figure 11:
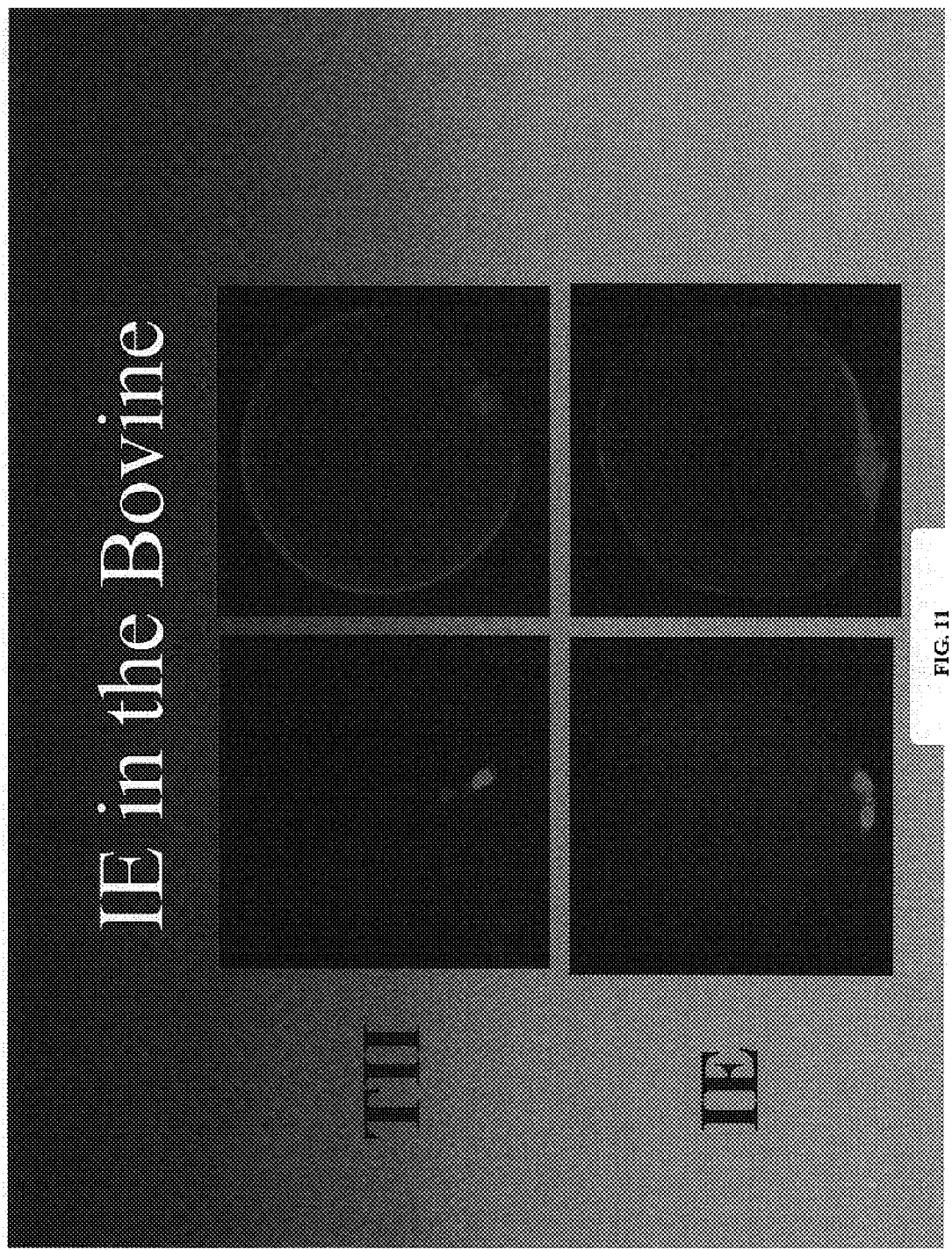
FIG. 11 is a series of color photographs showing bovine oocytes that have been subjected to induced enucleation by demecolcine using the methods of the present invention, and control Telophase II bovine oocytes.

FIG. 11 is a series of color photographs showing bovine oocytes that have been subjected to induced enucleation by demecolcine and control Telophase II bovine oocytes. In FIG. 11, the extrusion of the second PB in bovine oocytes has ceased. Prior to cessation of the formation of the second PB, the nucleus of a donor cell can be introduced into the oocyte to obtain a nuclear transfer embryo.

Example 4

Induced Enucleation of Mouse and Goat Oocytes Kinetic and Phenotypic Characterizations In general, the rates of successful somatic cell cloning of animals are poor, in part due to low efficiency in the production of competent cytoplasts when prepared by mechanical enucleation of MII oocytes. A method to induce enucleation of activated oocytes has been developed that supports enhanced rates of development of cloned mice to term. This study was designed to characterize the kinetics and progressive phenotypes observed during induced enucleation (IE) of activated mouse and goat oocytes. In vivo ovulated mouse oocytes (B6D2F1, n-959; CF 1, n=999) and in vitro matured goat oocytes (n-163) were denuded activated (7% ethanol) and incubated for up to 3.5 hr in KSOM. Enucleation was induced by continuous exposure to demecolcine (0.4 g/ml) commencing at 0-30 min post-activation. Non-demecolcine treated activated oocytes served as controls (n=50/rep). At selected time points oocytes (n=11.50) were fixed/extracted and processed for immunofluorescence microscopy to document activation and meiotic progression based on spindle (microtubules), chromatin (H33258) and polar body (PB. microfilaments) phenotypes. In mouse oocytes, activation rates were high and similar in both strains (89-10096). In contrast, the pace of meiotic progression and PB extrusion was strain dependent. Maximum IE rates (23-100%) were observed when oocytes were exposed to demecolcine immediately after activation, and the efficiency was also strain-dependent. IE rates diminished progressively when demecolcine treatment was delayed with respect to the time of activation. A range of distinct spindle, chromatin, PB and oocyte phenotypes were observed in response to demecolcine. In goat oocytes, activation was evident by anaphase onset at 30 min and activation rates of 69-94% were observed. When treated continuously with demecolcine from 30 thin post-activation, 63% of activated oocytes displayed all nuclear chromatin within the extruding second PB. Unlike the mouse, spindle, chromatin, PB and oocyte phenotypes displayed little variation. These results demonstrate that the IE method can be successfully employed to produce enucleated mouse and goat cytoplasts and therefore has broad utility for somatic cell cloning in many animal species.

Figure 12:
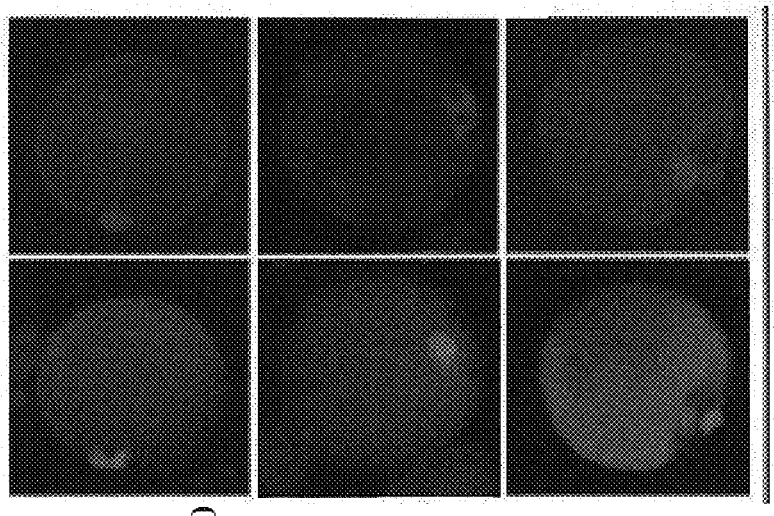
FIG. 12 is a graphical representation showing the rates of activation and the second PB extrusion in goat oocytes upon treatment with demecolcine.
Figure 12:
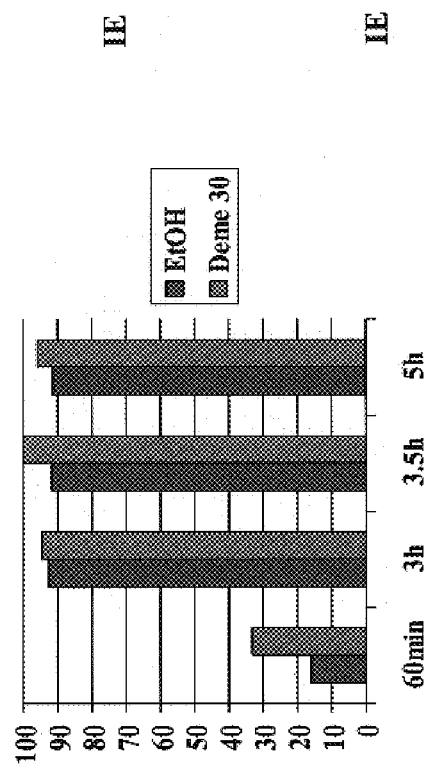

FIG. 12 shows a series of color photographs showing goat oocytes that have been subjected to induced enucleation by demecolcine, and control Telophase II bovine oocytes. In FIG. 12, the extrusion of the second PB in goat oocytes has ceased. Prior to cessation of the formation of the second PB, the nucleus of a donor cell can be introduced into the oocyte prior to obtain a nuclear transfer embryo, as described herein.

The teachings of all the patents, patent applications and publications cited herein are incorporated by reference in their entirety. In particular, U.S. patent application Ser. No.: 09/432,906, filed Nov. 2, 1999, entitled, "Methods for Cloning Animals," by Baguisi et al. is incorporated herein by reference in its entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of forming a nuclear transfer embryo, comprising the steps of:
    a) destabilizing microtubules of an oocyte, whereby all endogenous nuclear chromatin collects at a second polar body during meiosis of said oocyte; and
    b) combining the oocyte with at least the nucleus of a donor cell of the same species of said oocyte before a protrusion of the second polar body containing all of the endogenous nuclear chromatin ceases, thereby forming a nuclear transfer embryo containing the nucleus of the donor cells wherein the endogenous nuclear chromatin of the oocyte is in the second polar body.

2. The method of claim 1, wherein the microtubules are destabilized by combining the oocyte with a chemical selected from the group consisting of demecolcine, paclitaxel, phalloidin, coichicine, and nocodozole.

3. The method of claim 2, further includes activating the oocyte prior to exposing the oocyte to said chemical.

4. The method of claim 1, wherein the microtubules are destabilized by exposing the microtubules to electromagnetic radiation.

5. The method of claim 4, wherein the electromagnetic radiation is selected from the group consisting of x-rays and heat.

6. The method of claim 1, wherein the microtubules are destabilized by exposure of the oocyte to a change in pH or osmolality.

7. The method of claim 1, wherein the oocyte is in a telophase II or anaphase II stage of meiosis.

8. The method of claim 1, wherein the oocyte is in a metaphase II stage of meiosis.

9. The method of claim 8, further including the step of activating the oocyte.

10. The method of claim 1, wherein the donor cell is an activated donor cell.

11. The method of claim 10, wherein the activated donor cell is in the G1 stage of a mitotic cell cycle.

12. The method of claim 11, wherein the activated donor cell is a fibroblast activated donor cell.

13. The method of claim 12, wherein the somatic activated donor cell is an epithelial activated donor cell.

14. The method of claim 1, wherein the donor cell is a somatic cell.

15. The method of claim 14, wherein the donor cell is an adult somatic cell.

16. The method of claim 14, wherein the donor cell is an embryonic somatic cell.

17. The method of claim 1, wherein the oocyte is mammalian.

18. The method of claim 1, wherein the donor cell is transgenic.

19. The method of claim 10, wherein the compound that destabilizes the microtubules is selected from the group consisting of demecolcine, nocodazole, colchicine, phalloidin and paclitaxel.

20. A method of forming a non-human, mammalian nuclear transfer embryo, comprising the steps of:
    a) destabilizing microtubules of an oocyte, whereby all endogenous nuclear genetic material collects at a second polar body during meiosis of said oocyte; and
    b) combining the oocyte with at least the nucleus of a donor somatic cell of the same species of said oocyte before protrusion of the second polar body containing all of the endogenous nuclear chromatin ceases, thereby forming a nuclear transfer embryo.

* * * * *

UNITED STATES PATENT AND TRADEMARK OFFICE
CERTIFICATE OF CORRECTION

PATENT NO. : 7,612,250 B2
APPLICATION NO. : 10/208653
DATED : November 3, 2009
INVENTOR(S) : Eric W. Overstrom and Daniela Fischer Russell It is certified that error appears in the above-identified patent and that said Letters Patent is hereby corrected as shown below:

Claim 1, Column 29, Line 29 delete "cells" and insert --cell,--

Claim 2, Column 29, Line 34 delete "coichicine" and insert --colchicine--

Claim 11, Column 30, Line 13 delete "Gl" and insert --$G_1$--

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO.      : 7,612,250 B2                                         Page 1 of 1
APPLICATION NO. : 10/208653
DATED           : November 3, 2009
INVENTOR(S)     : Overstrom et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this

Nineteenth Day of October, 2010

David J. Kappos
*Director of the United States Patent and Trademark Office*